United States Patent
Kajiwara et al.

(10) Patent No.: US 9,291,604 B2
(45) Date of Patent: Mar. 22, 2016

(54) METHOD FOR MEASUREMENT OF VIBRATION PROPERTY OF STRUCTURE, AND VIBRATION PROPERTY MEASUREMENT DEVICE

(75) Inventors: Itsuro Kajiwara, Hokkaido (JP); Naoki Hosoya, Saitama (JP)

(73) Assignees: NATIONAL UNIVERSITY CORPORATION HOKKAIDO UNIVERSITY, Sapporo-Shi, Hokkaido (JP); SHIBAURA INSTITUTE OF TECHNOLOGY, Tokyo (JP)

( * ) Notice: Subject to any disclaimer, the term of this patent is extended or adjusted under 35 U.S.C. 154(b) by 552 days.

(21) Appl. No.: 13/704,439

(22) PCT Filed: Jun. 15, 2011

(86) PCT No.: PCT/JP2011/003412
§ 371 (c)(1),
(2), (4) Date: Dec. 14, 2012

(87) PCT Pub. No.: WO2011/158503
PCT Pub. Date: Dec. 22, 2011

(65) Prior Publication Data
US 2013/0090868 A1    Apr. 11, 2013

(30) Foreign Application Priority Data
Jun. 15, 2010   (JP) ................. 2010-136185

(51) Int. Cl.
| | |
|---|---|
| *G01F 17/00* | (2006.01) |
| *G01N 29/36* | (2006.01) |
| *G01M 5/00* | (2006.01) |
| *G01M 7/00* | (2006.01) |

(52) U.S. Cl.
CPC ............. *G01N 29/36* (2013.01); *G01M 5/0066* (2013.01); *G01M 5/0075* (2013.01); *G01M 5/0091* (2013.01); *G01M 7/00* (2013.01)

(58) Field of Classification Search
None
See application file for complete search history.

(56) References Cited

U.S. PATENT DOCUMENTS 5,827,971 A * 10/1998 Hale et al. ................. 73/657
2001/0032514 A1 * 10/2001 Maruyama ................. 73/657

FOREIGN PATENT DOCUMENTS

JP   2005-338063 A   12/2005

OTHER PUBLICATIONS

Hosoya, N., et al., "Vibration Testing Based on Impulse Response Excited by Laser Ablation", Transactions of the Japan Society of Mechanical Engineers, 75, 760, pp. 32-39, (2009).
Hosoya, N. et al., "Vibration Testing by Using Laser Ablation (Improvement of Accuracy in FRF measurement)", Dynamics and Design Conference, No. 09-23, 604 (2009).
Aoki, K., et al. "The study on the efficiency of projectile propulsion driven by laser ablation", Aerospace Numerical Simulation Symposium 2001 Ronbunshu, pp. 245-250, (2002).

* cited by examiner

*Primary Examiner* — Aditya Bhat
(74) *Attorney, Agent, or Firm* — Nath, Goldberg & Meyer; Tanya E. Harkins

(57) ABSTRACT

A method for generating vibration and measuring vibration properties of a structure, such as information equipment, micro-electrco/mechanical systems, and large-equipment, using a non-contact type laser excitation in a non-contact type vibration property measurement system.

2 Claims, 28 Drawing Sheets

METHOD FOR MEASUREMENT OF VIBRATION PROPERTY OF STRUCTURE, AND VIBRATION PROPERTY MEASUREMENT DEVICE

This is a National Phase Application filed under 35 U.S.C. 371 as a national stage of PCT/JP2011/003412, filed Jun. 15, 2011, and claims priority from the Japanese Application No. 2010-136185, filed Jun. 15, 2010, the content of each of which is hereby incorporated by reference in its entirety.

TECHNICAL FIELD

The present invention relates to a method and an apparatus that measure the vibration properties, for example, frequency response function (hereinafter abbreviated as "FRF") of a structure by non-contact type laser excitation.

BACKGROUND ART

In various mechanical systems, in order to evaluate the performance and reliability of a structure, it is indispensable to measure vibration properties. For example, it is necessary to perform measurement of vibration properties in vibration measurement of information equipment (head actuator mechanism of hard disk drives (HDD) or the like), MEMS (Micro Electro Mechanical Systems), or the like, and actual operation of large-sized equipment (cars or the like).

In recent years, MEMS that is a device that is produced using semiconductor ultra-fine processing technology or the like and has versatile functions integrated therein has attracted attention. For example, a MEMS device is mounted on an accelerometer, a pressure sensor, an air flow sensor, and the like as various sensors for cars or medical applications. As various sensors and actuators using the MEMS technology are developed from now on, development for application to optical communication and mobile equipment, application to peripheral devices of a computer, and application to bio-analysis and portable power sources is expected.

On the other hand, the MEMS device has a fine structure and the technology of inspecting the device properly is also important. For this reason, high-precision vibration measurement technology in a broad frequency band/high-frequency band is required.

In order to measure the vibration properties of a structure, FRF is obtained by applying an impulse input (for example, impulse excitation force) to the structure and measuring an input and an output. The methods that have become generally widespread for applying the impulse input to the structure are a method of attaching an excitation machine or the like separately and applying an impulse excitation force in a contact manner, a method of performing striking using an impulse hammer, and the like.

In measurement of the vibration properties of the structure, an input sensor and an output sensor are arranged in contact with the structure in order to measure the input and output when the impulse input is applied to the structure. A load cell is included in examples of the input sensor. An accelerometer is included in examples of the output sensor. Additionally, non-contact type sensors, such as a laser Doppler vibrometer and a laser displacement gage, are also included in examples of the output sensor.

In recent years, in order to apply the impulse input (impulse excitation force) to the structure, irradiating the structure with a laser beam and generating ablation have also been suggested (refer to NPL 1). According to impulse excitation using ablation, an excitation force in a high-frequency band can be applied to the structure. However, even in the method reported in NPL 1, it is necessary to arrange an input sensor for measuring the impulse excitation force in the structure.

CITATION LIST

Patent Literature

NPL 1
Naoki Hosoya, Itsuro Kajiwara, Hitoshi Sorimachi, "Vibration Testing Based on Impulse Response Excited by Laser Ablation", Collected Papers of Japan Society of Mechanical Engineers (Edition C), Volume 75, No. 760, and pp. 3160 to 3167

SUMMARY OF INVENTION

Technical Problem

As mentioned above, in order to measure the input and output when an impulse input is applied to the structure, it is necessary to arrange an input sensor and an output sensor in contact with the structure. If the input sensor and the output sensor are arranged on the structure, since the vibration of these sensors and the vibration of the structure may overlap each other and the vibration properties of the structure during actual operation may fluctuate, there is a case where vibration properties peculiar to the structure cannot be accurately measured. Additionally, if the input sensor and the output sensor are arranged on the structure, since a measurement system becomes large-sized, vibration measurement of a micro or lightweight structure as in MEMS cannot be realized.

Previous MEMS testing methods include, for example a method of 1) directly exciting a pedestal on which a minute structure after packaging is placed using an impulse hammer, 2) obtaining the amount of displacement from a movable part of the minute structure that is displaced by excitation, 3) determining mechanical properties, such as a damping ratio from the amount of displacement obtained, and 4) determining quality by the comparison between a threshold value and a measurements value. In such a striking test by an impulse hammer or the like, a low frequency band or a mid-frequency band of about several kilohertz is adopted as an object to be measured. Therefore, a vibration experiment for the minute structure that has a natural frequency in a high-frequency band is impossible. Additionally, it is very difficult to detect minute defects of the minute structure with high sensitivity, and it cannot be said that reliability regarding abnormal detection is sufficient.

Thus, an object of the invention is to provide a method for measuring vibration properties of a structure by applying an impulse input, specifically, provide a non-contact type vibration property measurement method that does not need an input sensor to be brought into contact with a structure, preferably, does not need an input sensor and an output sensor to be brought into contact with the structure.

Solution to Problem

The invention is characterized by measuring the vibration properties of a structure by experimentally normalizing the relationship between laser intensity and an impulse input induced by laser, thereby omitting arrangement of an input sensor to a structure that is an object to be measured, in a case where the impulse input (impulse excitation force or impulse excitation sound pressure) by the laser is applied to measure the vibration properties of the structure.

The present inventors have studied experimentally normalizing the relationship between laser intensity and an impulse input by laser by a rigid pendulum method. Moreover, the inventors have studied a method of estimating the application time at which the impulse input by laser is applied in actual measurement. Thereby, the present inventors have developed a method of calculating frequency response between input and output by measurement of only output from the magnitude of the impulse input and property correction according to the application time of the impulse input.

That is, the invention relates to a vibration property measurement method described below.

[1] A method for measuring vibration properties of a structure by applying an impulse input to the structure, including step (A) of pulse-irradiating the surface of the structure or the vicinity of the surface with a laser beam to apply an impulse input to the structure and measuring a response output from the structure to which the impulse input has been applied; step (B) of determining the relationship between the laser intensity of the laser beam and the impulse input induced by the laser beam by a rigid pendulum method and determining an impulse input F corresponding to the laser intensity of the laser beam, with which the structure has been pulse-irradiated, on the basis of the relationship; and step (C) of measuring the amplitude value of frequency response of the structure from the response output measured in step (A) and the impulse input F measured in step (B).

[2] The measurement method according to [1], wherein an application time L at which the impulse input has been applied to the structure is determined in step (A), and FRF of the structure is measured in step (C) from the response output and the application time L measured in step (A) and the impulse input F determined in step (B).

[3] The measurement method according to [1] or [2], wherein the impulse input is an impulse excitation force that is applied to the structure by pulse-irradiating the laser beam to the surface of the structure and generating ablation.

[4] The measurement method according to [1] or [2], wherein the impulse input is an impulse excitation sound pressure that is applied to the structure by pulse-irradiating the laser beam to the vicinity of the structure and generating breakdown.

[5] The measurement method according to [3], wherein in step (B), the relationship between the laser intensity of the laser beam, and the impulse input induced by the laser beam is determined on the basis of Newton's second law from a power spectrum corresponding to the magnitude of the acceleration of a rigid body block when the surface of the rigid body block is irradiated with the laser beam to generate ablation, and the mass of the rigid body block.

[6] The measurement method according to [4], wherein in step (B), the relationship between the laser intensity of the laser beam, and the impulse input induced by the laser beam is determined on the basis of Newton's second law from a power spectrum corresponding to the magnitude of the acceleration of a rigid body block when the vicinity of the rigid body block is irradiated with the laser beam to generate breakdown, and the mass of the rigid body block.

[7] The measurement method according to any one of [1] to [6], wherein the response output measured in step (A) is measured by a contact type sensor that is attached to the structure or a non-contact type sensor that is not attached to the structure.

[8] The measurement method according to any one of [1] to [7], wherein the response output measured in step (A) is the acceleration response or velocity response of the structure.

[9] The measurement method according to any one of [1] to [8], wherein in step (C), the amplitude value of the frequency response of the structure is measured by dividing a complex Fourier spectrum of frequency and vibration amplitude obtained from the response output measured in step (A), by the impulse input F determined in step (B).

[10] The measurement method according to any one of [1] to [8], wherein in step (C), FRF of the structure is measured by dividing a complex Fourier spectrum of frequency and vibration amplitude obtained from the response output measured in step (A), by the impulse input F determined in step (B) and by correcting phase properties by the application time L determined in step (A).

[11] The measurement method according to any one of [1] to [10], wherein the frequency band of the frequency response includes a band of 10 kHz or more.

[12] The measurement method according to [1] to [11], wherein in step (A), the structure is arranged in a liquid, a gas, or a vacuum.

Additionally, the invention relates to a vibration property measurement device described below.

[13] A vibration property measurement device for measuring vibration properties of a structure that is an object to be measured by applying an impulse input to the structure, including: a support that supports the structure that is an object to be measured; a pulse laser oscillator that pulse-irradiates a pulse laser to the surface of the structure supported by the support or the vicinity thereof; and a sensor that measures the acceleration or velocity of the structure, wherein the pulse laser is radiated to the surface of the structure so as to generate ablation or radiated to the vicinity of the structure so as to generate breakdown.

Advantageous Effects of Invention

By virtue of the invention, the vibration properties, for example, FRF of a structure can be measured without bringing an input sensor into contact with the structure that is an object to be measured. That is, according to the invention, a non-contact excitation type measurement system without an input sensor that comes into contact with the structure can be realized. Thus, ground-breaking effects for vibration measurement of MEMS, measurement in a minimum space, or the like are brought about. Moreover, if the output sensor is also of a non-contact type, a more ground-breaking measurement system is realized. For example, according to the invention, vibration properties can be measured by exciting a thin structure, the inner surface of a tube body, or the like, by which it is difficult to perform excitation in the method of the related art.

DESCRIPTION OF EMBODIMENTS

Figure 1:
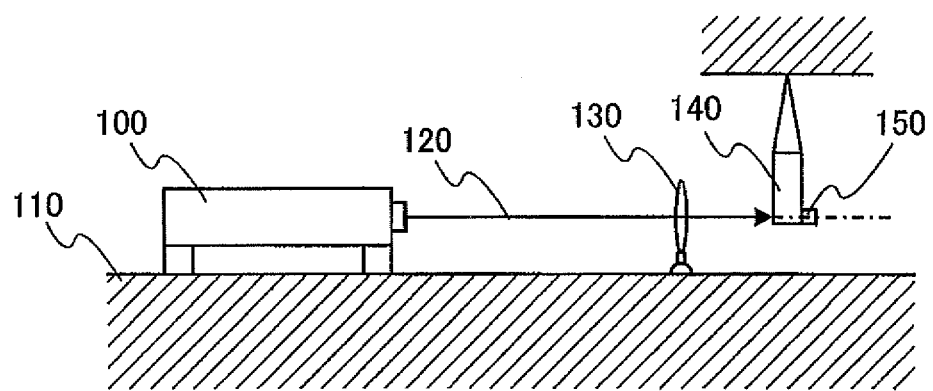
FIG. 1 is a schematic view showing the configuration of an impulse excitation system used in Example 1.

A method for measuring vibration properties in the invention applies an impulse input to a structure that is an object to be measured, to vibrate the structure, and determines the vibration properties of the structure from the relationship between the impulse input applied to the structure and the vibration of the structure. Here, not by actually measuring the impulse input that is applied to the structure but by separately determining the impulse input beforehand or afterwards, it becomes unnecessary to arrange an input sensor (a sensor that measures the impulse input) at the structure.

By pulse-irradiating the surface of the structure or its vicinity with a laser beam, the impulse input can be applied to the structure. In a case where the surface of the structure is pulse-irradiated with a laser beam, laser ablation (LA) occurs on the surface of the structure. As a result, the impulse excitation force induced by LA is applied to the structure as the impulse input. On the other hand, in a case where a space in the vicinity of the structure is pulse-irradiated with a laser beam, laser-induced breakdown (LIB) occurs in the space in the vicinity of the structure. As a result, impulse excitation sound pressure induced by LIB is applied to the structure as the impulse input.

The impulse excitation force induced by LA and the impulse excitation sound pressure induced by LIB have higher reproducibility than an excitation force induced by striking using an impulse hammer or the like. This is because the laser oscillation has high stability and also has high reproducibility. For this reason, even if the impulse excitation force induced by LA or the impulse excitation sound pressure induced by LIB is not actually measured, the impulse excitation force or impulse excitation sound pressure can be estimated by an experiment that is performed separately. Accordingly, it is unnecessary to attach an input sensor for measuring the impulse input to the structure.

The impulse input that is applied to the structure can be estimated by using a rigid pendulum method. Specifically, the relationship between laser intensity and an impulse input induced by LA or LIB is normalized, and the impulse input is calculated from the laser intensity of a laser beam radiated to the structure on the basis of the determined relationship.

The rigid pendulum method is a technique of applying an impulse input (impulse excitation force or impulse excitation sound pressure) to an excitation point of a suspended rigid body block and measuring the amplitude at that time. The impulse input generated by LA or LIB is calculated from the acceleration of the measured vibration and the mass of the rigid body block. The impulse input is calculated for every laser intensity, and the relationship between the laser intensity and the impulse input is normalized. In a case where the impulse input (impulse excitation force or impulse excitation sound pressure) is applied to the rigid body block (mass is defined as m) that is an object in a suspended free state, the relationship among the magnitude F of a force, acceleration A, and mass M according to Newton's second law becomes F=mA. That is, if the acceleration A of the rigid body block is measured, a power spectrum is obtained, and the mass m of the rigid body block is determined, the magnitude F of the force will be known.

As a specific procedure, a power spectrum $A(\omega)$ corresponding to the magnitude of the acceleration of the rigid body block is measured. Here, $\omega$ is angular frequency and the power spectrum represents the absolute value of the complex Fourier spectrum of an output obtained by measurement. At this time, if the excitation force induced by LA or the excitation sound pressure induced by LIB is used as an ideal impulse input, $A(\omega)$ in an ideal free state becomes a certain constant value A. Thus, the impulse input F applied to the structure that is an object to be measured is determined as F=mA.

The rigid body block to be used in the rigid pendulum method needs to have such a degree of rigidity that the rigid body block is not deformed by an impulse input induced by a laser beam. Additionally, it is desirable that the fundamental natural frequency of the rigid body block be sufficiently higher than a frequency band to be measured, specifically, more than double. For example, in a case where a frequency to be measured is set to more than 0 Hz and 50 kHz or less, the fundamental natural frequency of the rigid body block is set to 100 kHz or more. In a case where the fundamental natural frequency of the rigid body block is close to the frequency band to be measured, there is a concern that the calculation accuracy of the impulse input determined by the rigid pendulum method may deteriorate (refer to FIGS. 6A and 6B). The mass, moment of inertia, and center-of-gravity position of a rigid body block to be used are known.

Examples of the material of the rigid body block include metals, such as aluminum, and ceramics. Additionally, the size and mass of the rigid body block are set so as not to be influenced by the mass of an output sensor (accelerometer or the like) or its cable. Otherwise, the mass of the rigid body block may include the mass of an output sensor or its cable. The material of the structure that is an object to be measured and the material of the rigid body block may be the same.

In addition, in the rigid pendulum method, an impulse input may be applied to the rigid body block in a free state. The rigid body block may not be suspended. For example, the rigid body block may be placed on an air cushion (refer to Example 2).

Next, the surface of the structure that is an object to be measured or its vicinity is irradiated with a laser beam to generate LA or LIB, and an impulse input is applied to the structure. This generates vibration in the structure. At this time, it is not necessary to measure the impulse input applied. This is because the relationship between the laser intensity and the impulse input are separately determined as mentioned above, so that the impulse input can be determined from the laser intensity of the laser beam radiated to the structure that is an object to be measured. Accordingly, it is not necessary to attach input sensors (load cell or the like) for measuring the impulse input to the structure that is an object to be measured.

The laser beam to be radiated to the structure that is an object to be measured may be one that can generate LA on the surface of the structure or can generate LIB in the space in the vicinity of the structure. The type of laser is appropriately selected according to the type of the structure that is an object to be measured. For example, the laser may be a YAG laser. Additionally, the laser beam may be a pulse laser. The pulse width may also be selected according to the type of structure that is an object to be measured. For example, if the frequency band to be measured is set to a high-frequency band (normally 10 kHz or more, preferably 20 kHz or more, that is, several tens of kilohertz or more), a nanosecond laser is used. The strength of the laser beam is set to such a degree that the structure is not excessively damaged while generating LA or LIB. Since most of the energy of a laser is consumed for generation of plasma in a case where LIB is generated, the structure is hardly damaged. On the other hand, in a case where LA is generated, the structure is damaged, but damage to the structure does not affect the dynamic characteristic of the structure substantially.

The laser beam is condensed on the surface of the structure that is an object to be measured, or its vicinity through a condensing lens. An irradiation spot diameter in a condensing point is set so as to be several micrometers to several tens of micrometers. The incidence angle of the laser beam to the structure that is an object to be measured has a certain degree of freedom in setting, and may be set to an angle that satisfies the above irradiation spot diameter range. In the measurement method of the invention, the attachment position of the accelerometer that is an output sensor can be selected arbitrarily. Additionally, a non-contact type laser Doppler vibrometer, a non-contact type laser displacement gage, or the like can also be used as the output sensor. By virtue of the degree of freedom in setting of the incidence angle of the laser beam and selection of the aspect of the output sensor, measurement of the vibration properties of a minute structure is possible and measurement of the vibration properties of a region where measurement is difficult is also possible.

The response output (for example, acceleration response, velocity response, or the like) of the structure on which the impulse input induced by the laser beam has acted is measured by the output sensor. For example, the acceleration induced by the vibration of the structure is measured by the accelerometer. The accelerometer is directly brought into contact with the structure. The position where the accelerometer is arranged is not particularly limited, and may be a region that is intended to evaluate vibration properties.

The output sensor (for example, accelerometer) may be a non-contact type sensor that does not come into contact with the structure. The non-contact type sensor is a laser Doppler vibrometer, a laser displacement gage, or the like. If the non-contact type sensor is used as the output sensor, since it is then unnecessary to bring not only the input sensor but also the output sensor into contact with the structure, a perfect non-contact measurement system is realized.

A power spectrum of frequency and vibration amplitude is obtained from the response output (for example, acceleration response, velocity response, or the like) measured by the output sensor. By dividing a complex Fourier spectrum corresponding to the power spectrum by an impulse input F, the complex Fourier spectrum normalized by the magnitude of a force is determined. Thereby, an absolute value (amplitude ratio) in a frequency response is determined (refer to the following Formula (1)). Here, the impulse input F does not need to be an actual measurement value and may be calculated from the relationship between the laser intensity and the impulse input determined by the rigid pendulum method. The natural frequency of the structure can also be determined from the peak position of the power spectrum.

Figure 11A:
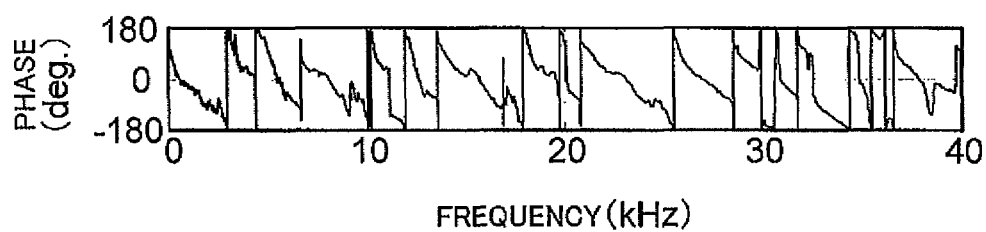
FIG. 11A is a graph showing phase properties before the correction of output by the complex Fourier spectrum.

By dividing the complex Fourier spectrum by the impulse input F, the complex Fourier spectrum normalized by the magnitude of a force is determined. However, since the application time of the impulse input influences the complex Fourier spectrum normalized by the magnitude of a force, the phase properties of the complex Fourier spectrum normalized by the magnitude of a force are not precise. An example of the phase properties by the complex Fourier spectrum in this stage are shown in FIG. 11A. As shown on the graph of FIG. 11A, it can be seen that the phase of a non-resonant region is delayed as the frequency becomes higher.

Figure 11B:
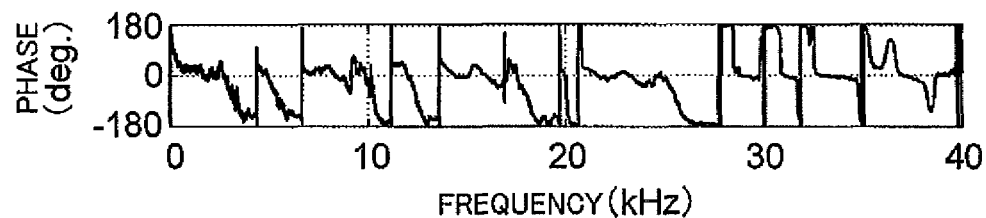
FIG. 11B is a graph showing phase properties corrected and obtained by the application time L of impulse force.

Thus, it is required to correct the complex Fourier spectrum corresponding to the power spectrum of frequency and vibration amplitude, using the application time L when the impulse input has acted on the structure that is an object to be measured. Specifically, since the frequency response of the application time is expressed by $e^{-j\omega L}$ (here, $j=\sqrt{-1}$), the complex Fourier spectrum is multiplied by the inverse ($e^{j\omega L}$) of the frequency response (refer to the following Formula (3)). FRF is determined by this. If the spectrum shown in FIG. 11A is corrected by the application time L, as shown on the graph of FIG. 11B, the phase of the non-resonant region becomes flat. Since the phase of the non-resonant region becomes flat by correcting the complex Fourier spectrum by the application time L in this way, the application time L that makes the phase of the non-resonant region flat is determined by repetition using an efficient algorithm.

By dividing the complex Fourier spectrum corresponding to the power spectrum by the impulse input F, and correcting the spectrum by the application time L, FRF can be determined. The sequence of the step of dividing the complex Fourier spectrum by the impulse input F and the step of correcting the complex Fourier spectrum by the application time L is not limited, and any step may first be performed.

In a case where the complex Fourier spectrum is divided by the impulse input F, the following Formula (1) is obtained. On the other hand, since the frequency response of the application time is expressed by $e^{-j\omega L}$, if the complex Fourier spectrum is corrected by the application time L, the following Formula (2) is obtained.

[Formula 1]
$$H_{ij}^{(A)}(\omega) = \frac{A_i(\omega)}{F_j} \quad (1)$$

[Formula 2]
$$H^{(P)}{}_{ij}(\omega) = e^{j\omega L} A_i(\omega) \quad (2)$$

Then, if the complex Fourier spectrum divided by the impulse input F is corrected by the application time L or if the complex Fourier spectrum corrected by the application time L is divided by the impulse input F, FRF shown in Formula (3) is obtained.

[Formula 3]
$$H_{ij}(\omega) = e^{j\omega L}\frac{A_i(\omega)}{F_j} \quad (3)$$

The FRF to be determined may be auto FRF and may be cross FRF. The auto FRF means FRF when an excitation point (input point) and a response point (output point) are the same, and the cross FRF means FRF when the positions of both the points are different.

The material of the structure in which vibration can be analyzed by the measurement method of the invention is not particularly limited. Examples of the material of the structure include organic materials, such as a resin material and a natural material (wood, natural fiber, or the like), inorganic materials, such as a nonmetal material (ceramics or the like) and a metal, and composite materials of organic materials and inorganic materials. In a case where the vibration properties of a material that is not a rigid body, such as rubber, are measured, in a step of determining the impulse excitation force, the impulse excitation force may be determined in a state where a rubber piece made of the same material is stuck on the laser irradiation surface of a rigid body block made of metal or the like. This is because a material that is not a rigid body is deformed when being irradiated with a laser beam, and an excitation force is not determined. It is preferable that the mass of a rigid body block to be used in the rigid pendulum method be regarded as the mass obtained by adding the mass of the stuck rubber piece or the like.

According to the method for measuring vibration properties in the invention, at least the input sensor attached to the structure can be made unnecessary. Moreover, if a non-contact type sensor is selected as the output sensor, the vibration properties of the structure can be precisely understood without bringing the input sensor and the output sensor into contact with the structure that is an object to be measured. Accordingly, the structure that is an object to be measured may be arranged in arbitrary media (for example, in liquids such as water, in gases such as air, or in a vacuum).

The method for measuring vibration properties in the invention may be applied to measurement of the vibration properties of all products. Particularly, since a measurement system of the invention is miniaturized, this is advantageous to vibration measurement or the like of MEMS. Of course, the method for measuring vibration properties in the invention also contributes to a countermeasure against vibration or noise of a washing machine that is a general home appliance, and studies for silencing of refrigerators or air-conditioners. Additionally, with respect to the tires of a car, for example, it is possible to exactly evaluate pattern noise resulting from a tread pattern or to evaluate the vibration properties of the tires during actual traveling. Additionally, the method for measuring vibration properties in the invention can also evaluate the vibration properties of underwater structures, such as an underwater robot, and an inflatable space structure made of a lightweight and flexible resin film or the like.

Moreover, in the method for measuring vibration properties in the invention, non-contact of input measurement or input/output measurement is possible. Therefore, testing in institutions and facilities where direct contact with people is difficult can also be safely and easily performed. For example, metal fatigue is one cause of accidents in aircraft, nuclear power stations, or the like. Particularly, the fatigue fracture in aircraft, nuclear generators, cars, trains, or the like may lead to a major accident that even threaten human lives. According to the invention, through a simple system, it is possible to detect malfunctions, such as fine metal fatigue, and prevent these major accidents in advance, by non-contact vibration analysis even in plant portions with a concern for radiation contamination.

A device for measuring vibration properties in the invention includes, for example, a support for supporting a structure that is an object to be measured, a pulse laser oscillator for pulse-irradiating a pulse laser to the structure supported by the support, and an accelerometer for measuring the acceleration of the structure. Of course, other arbitrary members are provided if necessary. Here, the pulse laser is characterized by being irradiated to the surface of the structure that is an object to be measured, to generate LA, or being irradiated to the vicinity of the structure, to generate LIB. The support for supporting the structure that is an object to be measured may support the structure in other arbitrary aspects, such as suspending the structure so as to be in a peripherally free state or fixedly supporting the structure.

EXAMPLES

Hereinafter, the method for measuring vibration properties in the invention will be described with reference to examples.

Example 1

In Example 1, an example in which the surface of a structure is irradiated with a laser beam and the impulse excitation force induced by LA is applied to the structure is described.

1. Impulse Excitation System

FIG. 1 is a schematic view showing the configuration of an impulse excitation system used in the present experiment. As shown in FIG. 1, a high-output YAG pulse laser 100 (Surelite II; made by Continuum Inc.; wavelength of 1064 nm, output of 0.65 J, and pulse width of 5 nanoseconds) was installed on an optical table 110. A laser beam 120 from the YAG pulse laser 100 was condensed on the surface of a structure 140 through a spherical biconvex lens 130 (SLB-30B-100P; Sigma Koki Co., Ltd.). The laser output of the high-output YAG pulse laser 100 was set to 0.21 J. Additionally, the spot diameter of the laser beam 120 on the surface of the structure 140 was set to 2 μm.

The structure 140 was peripherally freely supported by suspension. An accelerometer 150 (NP-3211; Ono Sokki Co., Ltd.; mass of 0.5 g, sensitivity of 1.004 mV (m/s$^2$), and natural frequency of 50 kHz or more) was attached to a measurement point of the structure 140 with an adhesive. Although the output sensor (accelerometer 150) was attached to the structure 140, the input sensor for measuring the excitation force was not attached.

On the surface of the structure 140, the impulse excitation force induced by LA was applied to the structure 140, to vibrate the structure 140. The acceleration in the vibration of the structure 140 was measured by the accelerometer 150. The acceleration measured by the accelerometer 150 was recorded using a spectrum analyzer (A/D: NI PXI-1042Q, PXI-4472 B; National Instruments Corporation, and software: CAT-System; Catec Inc.). The frequency to be measured was more than 0 Hz and 40 kHz or less.

Figure 2:
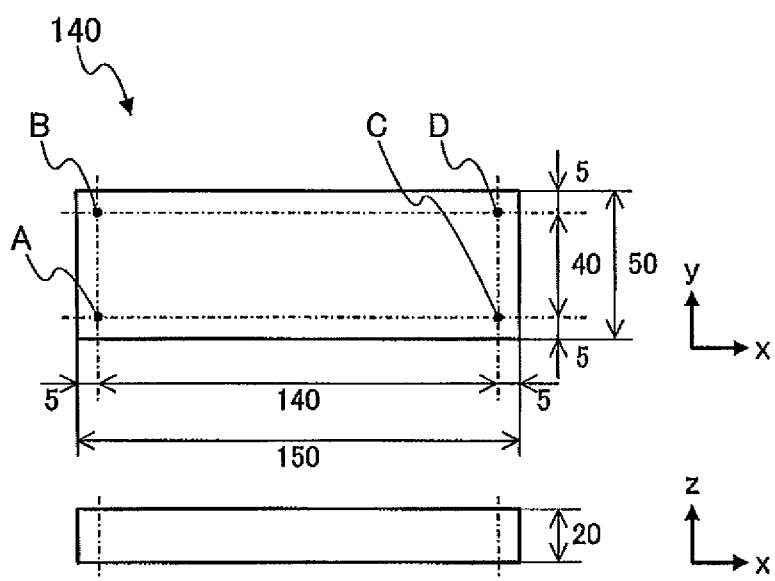
FIG. 2 is a plan view and side view of a structure used in Example 1.

FIG. 2 is the plan view and side view of the structure 140 used in the present experiment (unit: mm). As shown in FIG. 2, the structure 140 is a rectangular parallelepiped block (size: 150 mm×50 mm×20 mm and mass: 398 g) made of aluminum. The out-of-plane mode of the structure 140 was adopted as an object to be measured. Additionally, both the number of excitation points and the number of measurement points were set to four points (points A to D).

Eigenvalue analysis of the structure 140 was performed by Nastran (finite element method CAE software). A hexa solid element (mesh size: 1 mm, number of nodal points: 163082, and number of elements: 150250) was used as an FE model of the structure 140. The accelerometer 150 was taken into consideration in the hexa solid element. The results of the eigenvalue analysis of the structure 140 are shown in Table 1. As shown in Table 1, fourteen natural frequencies were confirmed within a range of a frequency-to-be-measured of more than 0 Hz and 40 kHz or less.

TABLE 1

Natural Frequency of Object Structure

| Order | Frequency [Hz] |
|---|---|
| 1st | 4398.8 |
| 2nd | 6703.7 |
| 3rd | 11095.0 |
| 4th | 13551.9 |
| 5th | 19562.1 |
| 6th | 20724.1 |
| 7th | 28381.9 |
| 8th | 30625.5 |
| 9th | 32205.4 |
| 10th | 32358.1 |
| 11th | 35163.1 |
| 12th | 36537.1 |
| 13th | 39449.9 |
| 14th | 39793.9 |

In order to calculate FRF by the finite element analysis (FEA), it is necessary to determine a modal damping ratio in advance. The modal damping ratio may be determined from a vibration experiment (experiment modal analysis). However, in the present experiment, with respect to FRF (calculation value) obtained by FEA and FRF (experimental value) obtained by experiment, the modal damping ratio was adjusted so that the calculation value of a resonant response level became close to the experimental value. The set modal damping ratio was within a range of 0.1 to 0.5%.

2. Normalization of Impulse Excitation Force by Rigid Pendulum Method

The relationship between laser intensity and impulse excitation force was normalized by the rigid pendulum method. First, a rigid body block 160 for normalizing the relationship between laser intensity and impulse excitation force by the rigid pendulum method was prepared. As the shape of the rigid body block 160, a cube with one side of 20 mm was used due to ease of attachment, acquisition, and manufacture of the accelerometer 170. Aluminum was used as the material of the rigid body block 160, similarly to the structure 140. The mass of the rigid body block 160 was 21.8 g when measured by an electronic balance (EK-3000i; made by A & D Company, Limited, resolution of 0.1 g).

Figure 3:
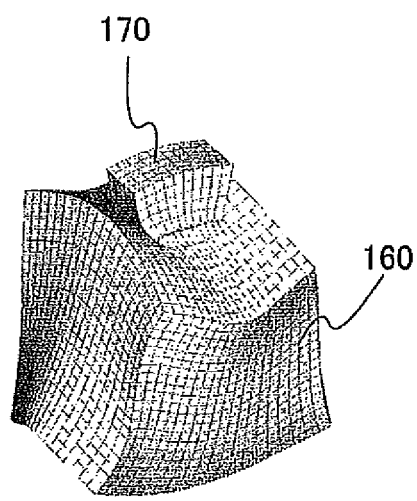
FIG. 3 is a view showing a primary vibration mode of a rigid body block used in Example 1.

The accelerometer 170 was attached to the rigid body block 160 with an adhesive. The accelerometer 170 is the same as the aforementioned accelerometer 150. The eigenvalue analysis of the rigid body block 160 was performed using Nastran. A hexa solid element (mesh size: 1 mm, number of nodal points: 10622, and number of elements: 8250) was used as an FE model of the rigid body block 160. The accelerometer 170 was taken into consideration as the hexa solid element. FIG. 3 is a view showing a primary vibration mode of the rigid body block 160. It could be confirmed that the primary natural frequency was 96695.3 Hz and was higher than 40 kHz that is the upper limit of the frequency to be measured.

Next, the impulse excitation force induced by LA was determined by the rigid pendulum method. The accelerometer 170 was attached onto the central axis of the rigid body block 160. The back side of the attachment position of the accelerometer 170 was adopted as the excitation point. A laser beam was condensed on the excitation point, the impulse excitation force induced by LA was applied to the rigid body block 160, and the acceleration response of the rigid body block 160 was measured.

Figure 4:
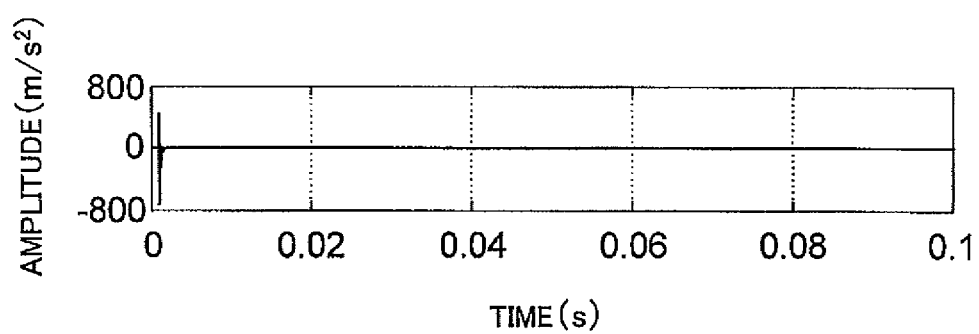
FIG. 4 is a graph showing the relationship between time and amplitude of the rigid body block, which is obtained by the rigid pendulum method.
Figure 5:
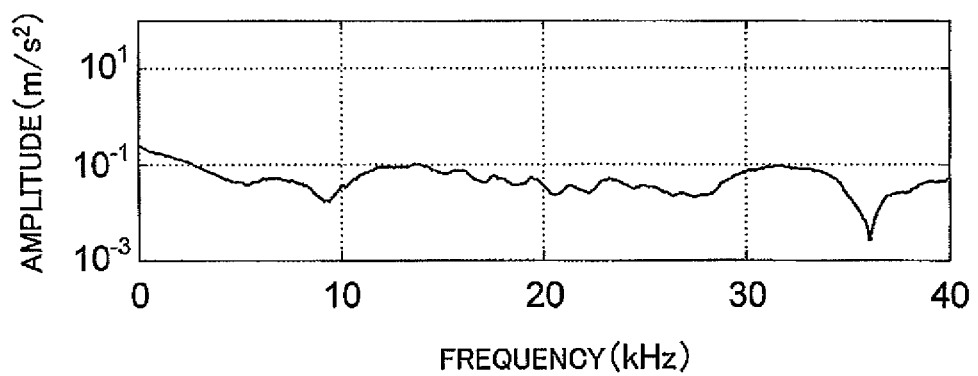
FIG. 5 is a graph showing the relationship between vibration frequency and amplitude of the rigid body block, which is obtained by the rigid pendulum method.

FIG. 4 is a graph (time history waveform) showing the relationship between time and amplitude of the rigid body block 160. FIG. 5 is a graph (power spectrum) showing the relationship between vibration frequency and amplitude of the rigid body block 160. It can be seen from FIG. 4 that the acceleration response of the rigid body block 160 becomes an ideal impulse. Although slight variation has occurred in the power spectrum of FIG. 5, the amplitude should essentially become constant regardless of the frequency. It is believed that the variation in the power spectrum of FIG. 5 is affected by the positional deviation of the excitation point (laser irradiation position) or measurement point, a supporting method using suspension, random error in measurement, the attachment state of the accelerometer, or the like. By averaging the impulse excitation force F(ω) obtained in the overall frequency band in a case where the laser output is 0.21 J, the impulse excitation force in a case where the laser output is 0.21 J was calculated to be 1.53 mN.

Figure 6A:
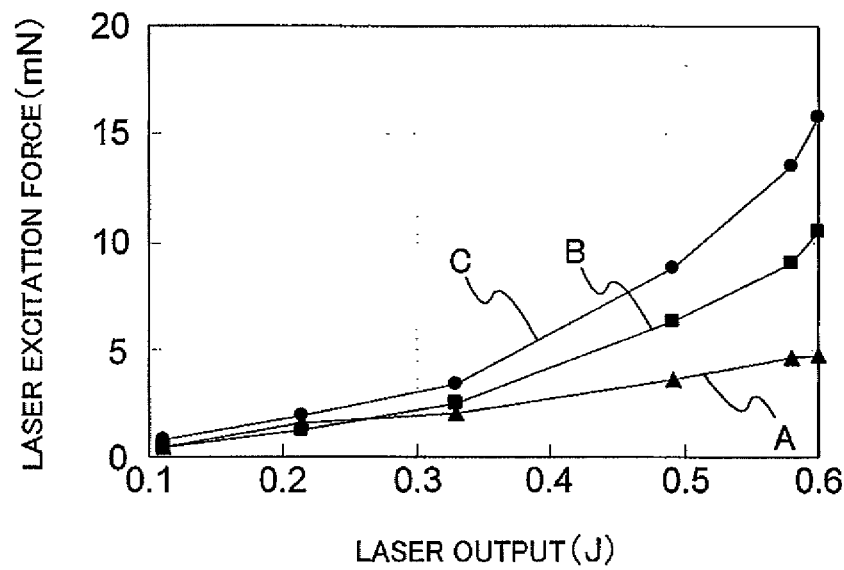
FIG. 6A is a graph showing the relationship between laser output and impulse excitation force.

FIG. 6A is a graph showing the relationship between laser output and impulse excitation force (laser excitation force). In FIG. 6A, curve A represents results when a rigid body block (primary natural frequency: 96695.3 Hz) with one side of 20 mm was used, curve B represents results when a rigid body block (primary natural frequency: 62627.6 Hz) with one side of 35 mm was used, and curve C represents results when a rigid body block (primary natural frequency: 44161.6 Hz) with one side of 50 mm was used. It can be seen from this graph that differences are caused in the impulse excitation forces due to the influence of the natural frequency of the rigid body blocks used. These differences become large with an increase in the laser output.

Figure 6B:
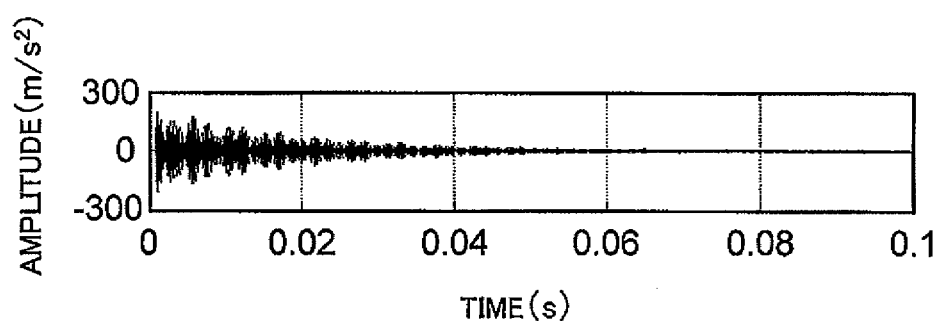
FIG. 6B is a graph showing the relationship between time and amplitude of the rigid body block when the rigid body block with one side of 50 mm is used.

FIG. 6B is a graph showing the relationship between time and amplitude of the rigid body block when the rigid body block with one side of 50 mm is used (laser output: 0.21 J). In a case where the rigid body block with one side of 20 mm (primary natural frequency: 96695.3 Hz) was used, the impulse waveform was observed as shown in FIG. 4. In contrast, in a case where the rigid body block with one side of 50 mm (primary natural frequency: 44161.6 Hz) was used, damped vibration induced by the elastic vibration of the rigid body block was confirmed as shown in FIG. 6B. This suggests that the natural frequency of the rigid body block has an influence on the calculation accuracy of the laser excitation force.

Additionally, the application time L to the rigid body block 160 of the impulse excitation force induced by LA was estimated to be 0.0013 seconds. The estimation of the application time L was determined by repetition using an efficient algorithm so that the phase of the non-resonant region of the complex Fourier spectrum corresponding to the power spectrum became flat.

3. Measurement of Auto FRF

Figure 7:
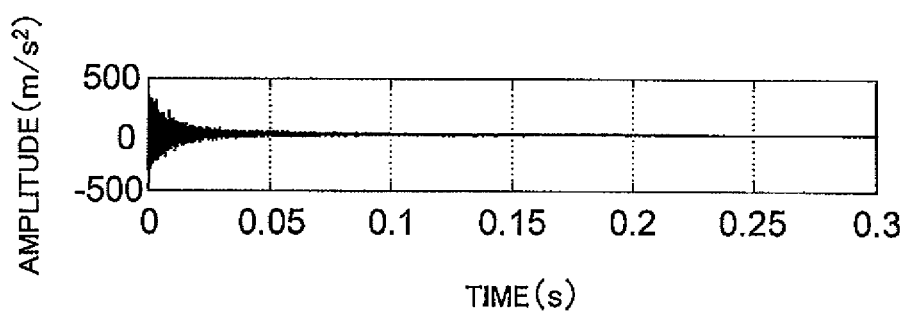
FIG. 7 is a graph showing the relationship between time and amplitude of the structure, which is measured in Example 1.
Figure 8:
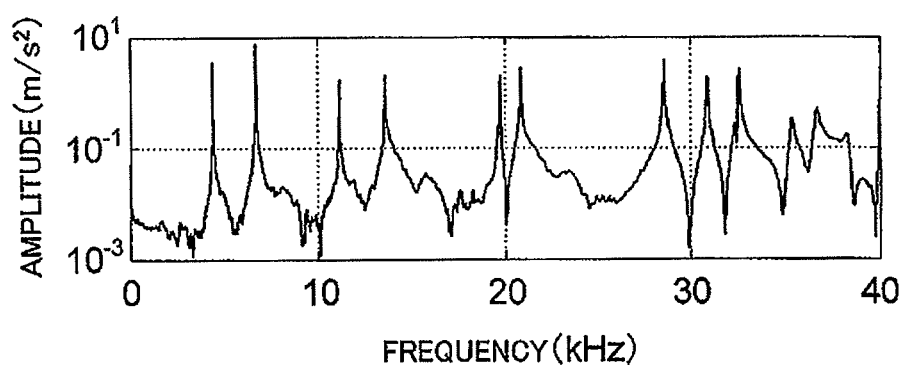
FIG. 8 is a graph showing the relationship between vibration frequency and amplitude of the structure, which is measured in Example 1.

The auto FRF of the structure 140 was measured using the impulse excitation system shown in FIG. 1. The laser beam 120 was condensed at point A of the structure 140 (refer to FIG. 2) to generate LA, and an impulse excitation force was applied to the structure 140 (laser output: 0.21 J). FIG. 7 is a graph showing the acceleration response of the structure 140 at this time. FIG. 8 is a graph showing a power spectrum at this time.

Figure 9A:
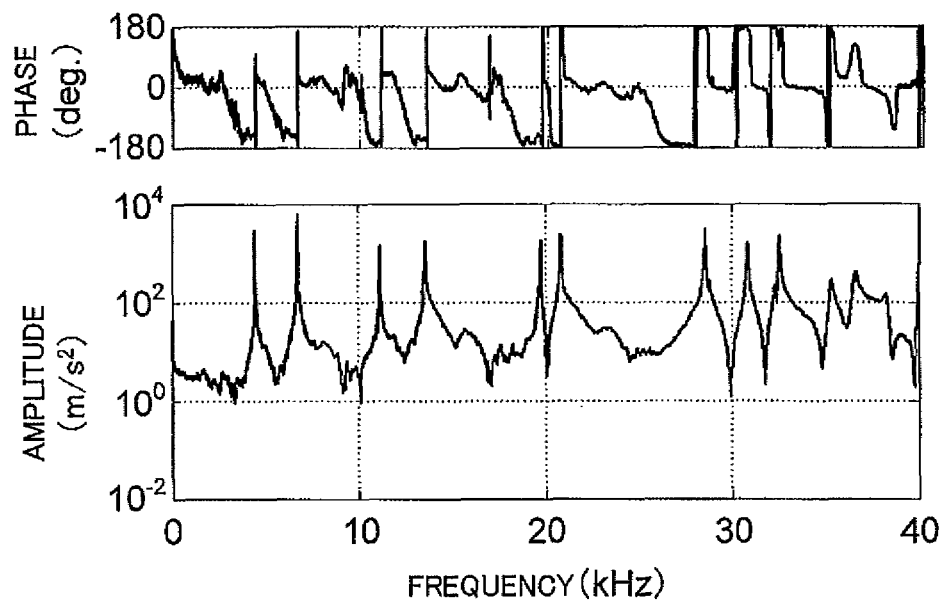
FIG. 9A is a graph showing auto FRF determined by the method of the invention.
Figure 9B:
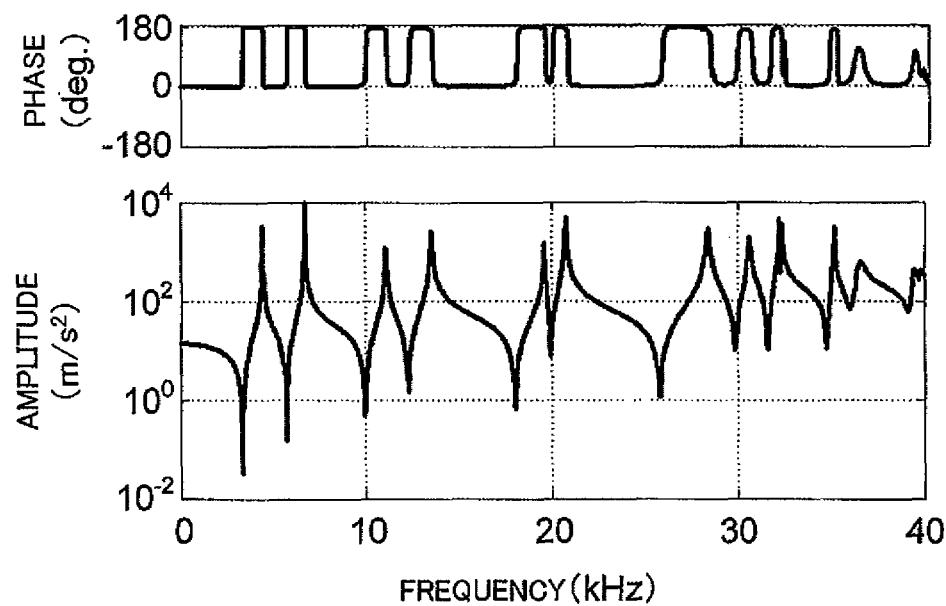
FIG. 9B is a graph showing auto FRF determined by the finite element analysis (FEA).

FIG. 9A is a graph showing auto FRF ($H_{A-A}$) obtained by dividing a complex Fourier spectrum corresponding to the graph of FIG. 8 by an impulse excitation force (1.53 mN) determined by the rigid pendulum method, and correcting properties by the application time of the impulse excitation force. FIG. 9B is a graph showing FRF determined by FEA for comparison with FIG. 9A. It can be seen that the phase of the complex Fourier spectrum normalized by the magnitude of a force shown in FIG. 11A is tilted downward to the right, whereas this can be corrected in FIG. 9A.

−180 degrees on the graph of FIG. 9A means the same phase as +180 degrees on the graph of FIG. 9B. That is, both phases are shifted by a half cycle with respect to an input. It can be seen that the phases are 90 degrees at resonant points on both the graphs of FIGS. 9A and 9B and the amplitude of FRF determined by the measurement method of the invention and the amplitude of FRF by FEA coincide with each other. Additionally, the surprising results that phase properties coincide with each other well even in a high-frequency band (frequency band of 20 kHz or more) that cannot be measured in the vibration experiment of the related art were obtained. On the graphs of FIGS. 9A and 9B, slight differences, such as different directions of delayed phases, may be recognized. However, this is believed to be due to the influence of the correction error and dead time measurement error.

4. Measurement of Cross FRF

Figure 10A:
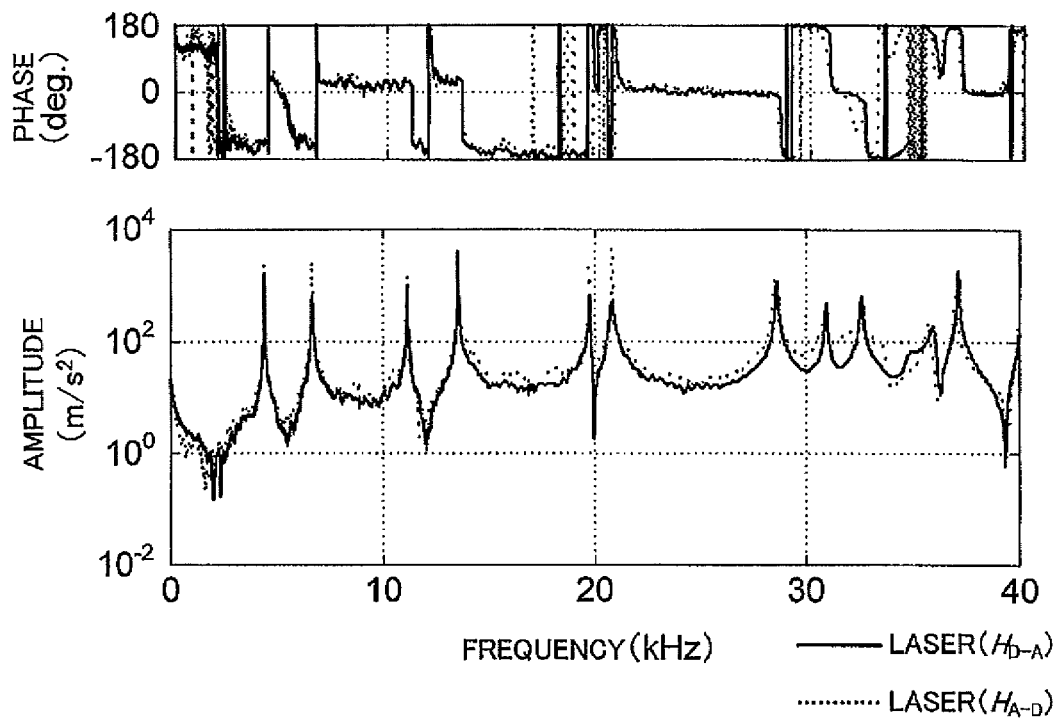
FIG. 10A is a graph showing cross FRF determined by the method of the invention.
Figure 10B:
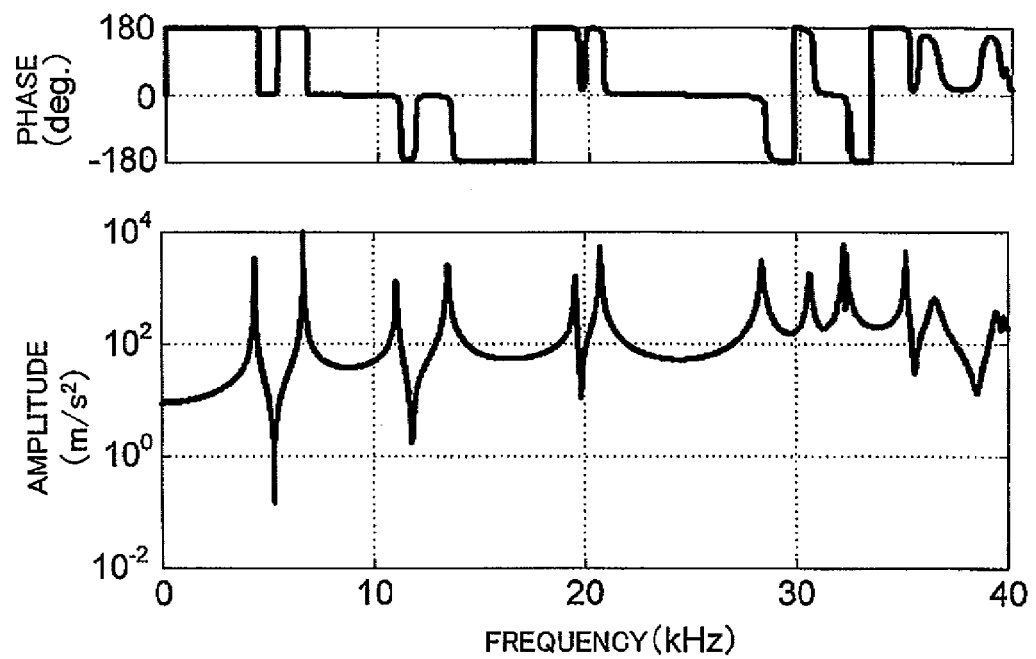
FIG. 10B is a graph showing cross FRF determined by FEA.

Next, the cross FRF ($H_{D-A}$) between points D-A of the structure 140 (refer to FIG. 2) and the cross FRF ($H_{A-D}$) between points A-D (refer to FIG. 2) are shown in FIG. 10A (solid line is $H_{D-A}$ and broken line is $H_{A-D}$). FRF determined by FEA is shown in FIG. 10B for comparison. As shown in FIG. 10A, the cross FRF ($H_{D-A}$) and the cross FRF ($H_{A-D}$) coincide with each other well. Since the same cross FRF is obtained even if the input point and the output point are exchanged with each other in this way, assumption of a linear system is satisfied and Maxwell's reciprocity theorem is established. For this reason, it can be seen that the reliability of FRF is high and the measurement method of the invention is effective in measurement of FRF. If assumption of a linear system is not satisfied, it can be said that the reliability of FRF is low and the measurement method is not suitable for measurement of FRF. In this case, it is believed that an experiment system apparatus or a test piece (aluminum block) has non-linearity, or the excitation force is insufficient.

Additionally, as can be seen from the comparison between FIG. 10A and FIG. 10B, it can be seen that the cross FRF determined by the method of the invention coincides with FRF by FEA well.

In this way, it can be seen that the FRF measurement of the invention, which normalizes the relationship between laser output and impulse excitation force, thereby determining the impulse excitation force that has been applied to the structure that is an object to be measured and that corrects properties by the application time of the impulse excitation force, thereby making the input sensor unnecessary, is effective.

Example 2

In Example 2, an example in which the surface of a structure in water is irradiated with a laser beam and the impulse excitation force induced by LA is applied to the structure is shown.

1. Impulse Excitation System

Figure 12:
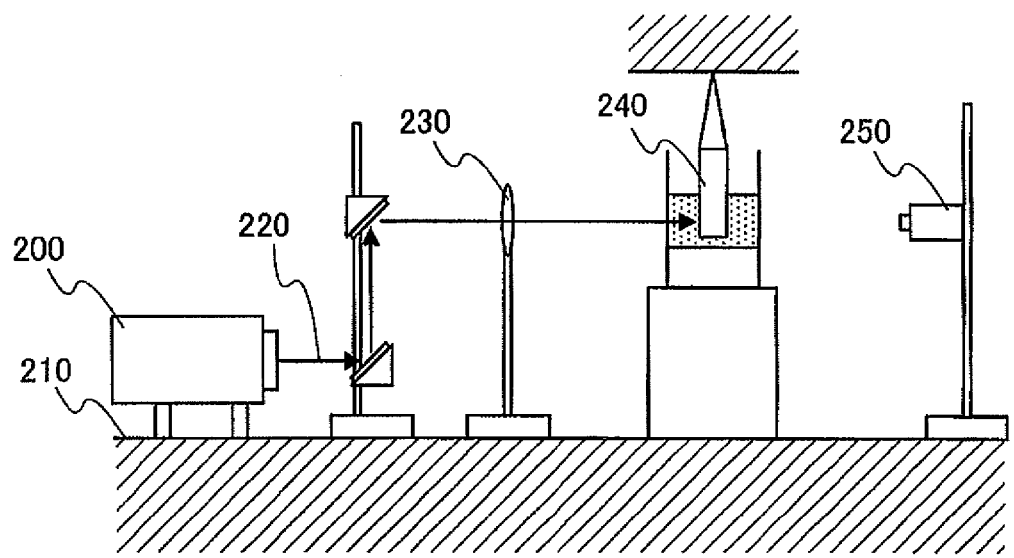
FIG. 12 is a schematic view showing the configuration of an impulse excitation system used in Example 2.

FIG. 12 is a schematic view showing the configuration of an impulse excitation system used in the present experiment. As shown in FIG. 12, a high-output YAG pulse laser 200 (Surelite III; made by Continuum Inc.; wavelength of 1064 nm, output of 1 J, and pulse width of 5 nanoseconds) was installed on an optical table 210. A laser beam 220 from the YAG pulse laser 200 was irradiated to the surface of a structure 240 through a spherical plano-convex lens 230 (SLB-30-200P; Sigma Koki Co., Ltd.). The laser output of the high-output YAG pulse laser 200 was set to 0.141 J. Additionally, the spot diameter of the laser beam 220 on the surface of the structure 240 was set to 2 μm.

The structure 240 was peripherally freely supported by suspension. Additionally, a lower half of the structure 240 was immersed in water. Water was held in a container made of acrylic (outside dimensions 101 mm×101 mm×101 mm, plate thickness of 2 mm).

The impulse excitation force induced by LA was applied to the structure 240, to vibrate the structure 240. The acceleration (differential value of velocity) at a measurement point of the structure 240 was measured using a laser Doppler vibrometer 250 (LV-1720; One Sokki Co., Ltd.). As shown in FIG. 12, the input sensor and the output sensor were not attached to the structure 240.

The velocity response measured by the laser Doppler vibrometer 250 was recorded using a spectrum analyzer (A/D: NI PXI-1042Q, PXI-4472 B; National Instruments Corporation, and software: CAT-System; Catec Inc.). The frequency to be measured was more than 0 Hz and 40 kHz or less.

Figure 13:
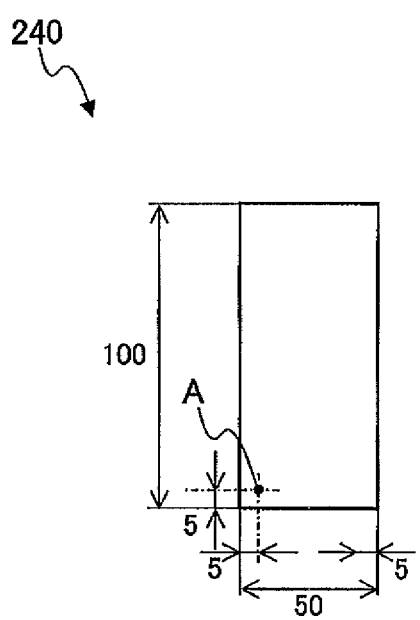
FIG. 13 is a plan view of a structure used in Example 2.

FIG. 13 is a plan view of the object structure 240 used in the present experiment (unit: mm). As shown in FIG. 13, the object structure 240 is a rectangular parallelepiped block (size: 100 mm×50 mm×5 mm) made of aluminum. The out-of-plane mode of the object structure 240 was adopted as an object to be measured. Additionally, both the excitation point and the measurement point were set to point A.

2. Normalization of Impulse Excitation Force by Rigid Pendulum Method

Figure 14:
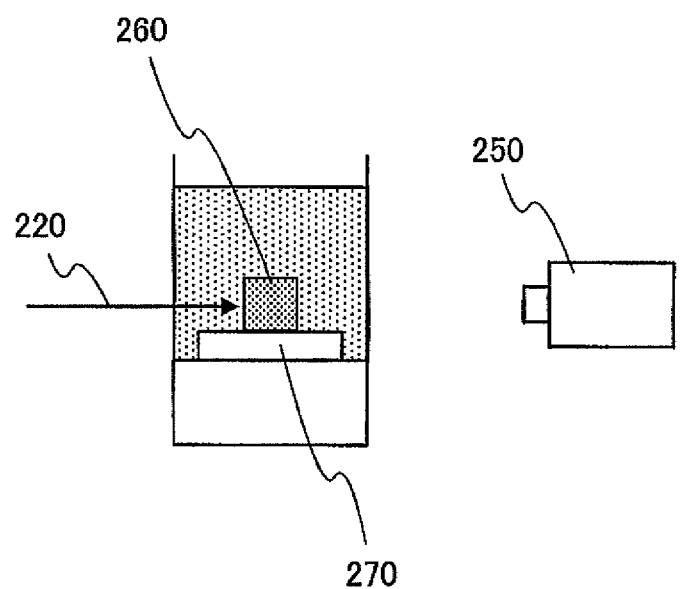
FIG. 14 is a view showing an aspect in which an impulse excitation force to a rigid body block in water is measured by the rigid pendulum method.

The relationship between laser intensity and impulse excitation force was normalized by the rigid pendulum method. First, a rigid body block 260 for normalizing laser intensity and impulse excitation force by the rigid pendulum method was prepared. An aluminum cube (with one side of 20 mm) was used as the rigid body block 260, similarly to Example 1. As shown in FIG. 14, the rigid body block 260 was freely supported in water by an air cushion 270.

Next, the impulse excitation force induced by LA was determined by the rigid pendulum method. The laser beam 220 was condensed on the excitation point on the central axis of the rigid body block 260, and the impulse excitation force induced by LA was applied to the excitation point of the rigid body block 260. Then, the velocity response of the measurement point on the back side of the excitation point of the rigid body block 260 was measured using the aforementioned laser Doppler vibrometer. As a result, the impulse excitation force at a laser output of 141 mJ was 23.7 mN.

3. Measurement of Auto FRF

The auto FRF of the structure 240 was measured using the impulse excitation system shown in FIG. 12. The laser beam 220 was condensed at point A of the structure 240 (refer to FIG. 13) to generate LA, and an impulse excitation force was applied to the structure 240.

Figure 15:
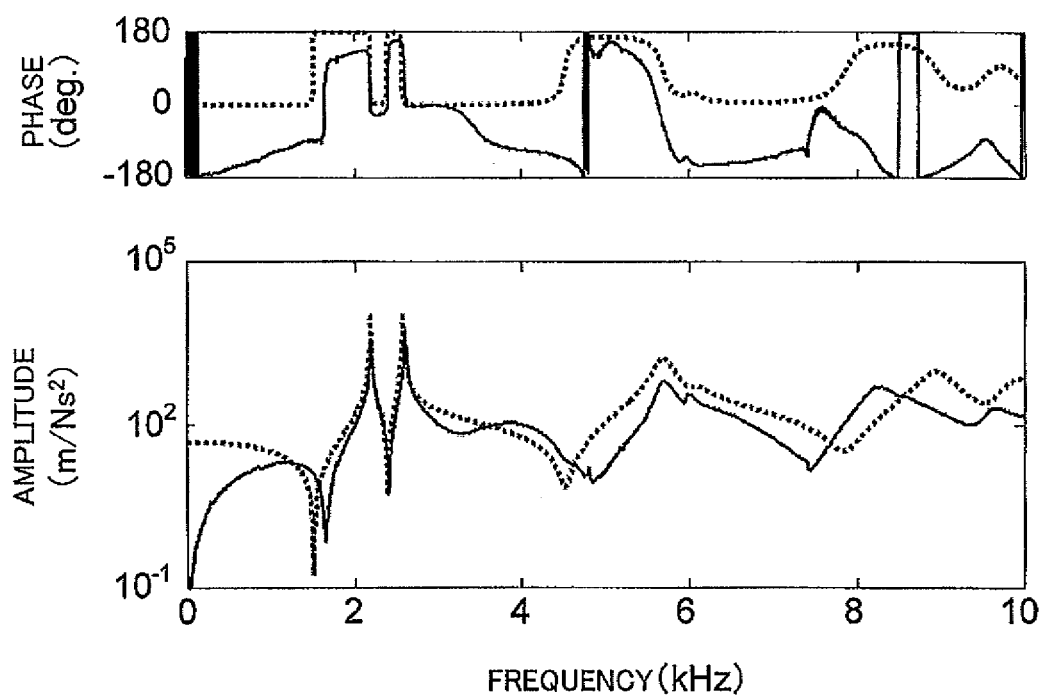
FIG. 15 is a graph showing auto FRF measured in a state where a structure is half-immersed in water by the method of the invention, and FRF determined by FEA.

FIG. 15 is a graph showing measured auto FRF ($H_{A-A}$) (solid line) and FRF ($H_{A-A}$) (broken line) determined by FEA. On this graph, the damping ratio of auto FRF determined by FEA is adjusted so that auto FRF determined by experiment and auto FRF determined by FEA coincide with each other. It can be seen from FIG. 15 that the amplitude of FRF determined by the method of the invention, and the amplitude of FRF by FEA substantially coincide with each other. It can be seen from this that FRF can be determined by the impulse excitation induced by LA also with respect to the structure in water.

Figure 16:
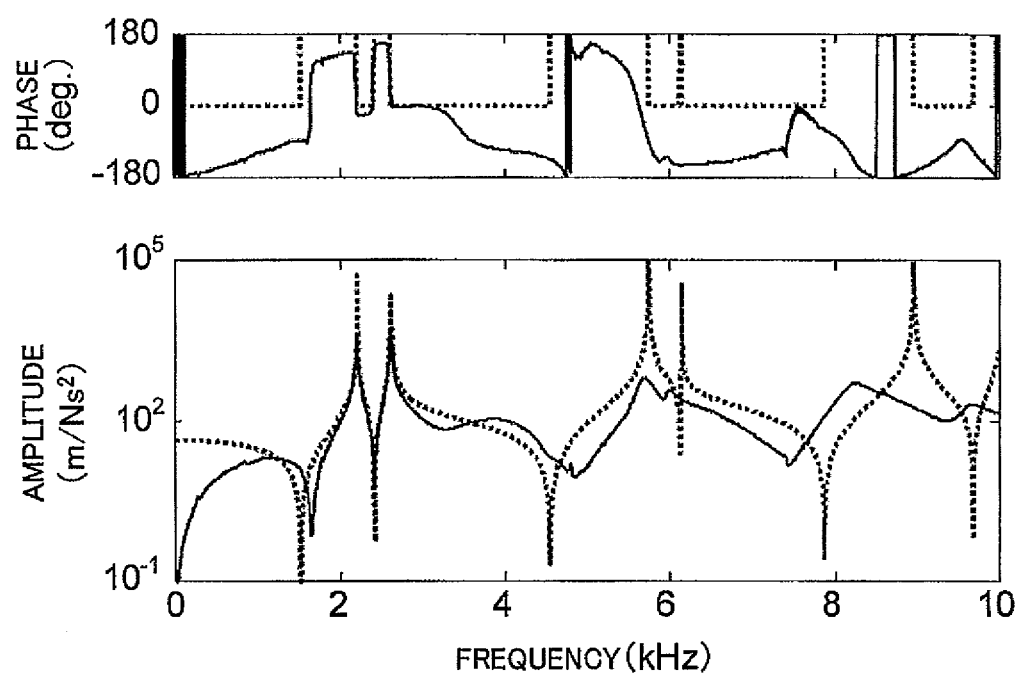
FIG. 16 is a graph showing auto FRF measured in a state where the structure is half-immersed in water by the method of the invention, and FRF determined by FEA.

FIG. 16 is a graph showing measured auto FRF ($H_{A-A}$) and FRF ($H_{A-A}$) determined by FEA. On this graph, the damping ratio of auto FRF determined by FEA is set to 0%. Referring to FIG. 16, the difference between the amplitude of the measured auto FRF and the amplitude of auto FRF determined by FEA becomes large with respect to all the natural frequencies. Since the vibration experiment of an underwater structure could not be performed in the vibration experiment of the related art, the damping ratio could not be experimentally identified. For this reason, correct auto FRF could not be determined by FEA in the related art unlike this graph.

Figure 17:
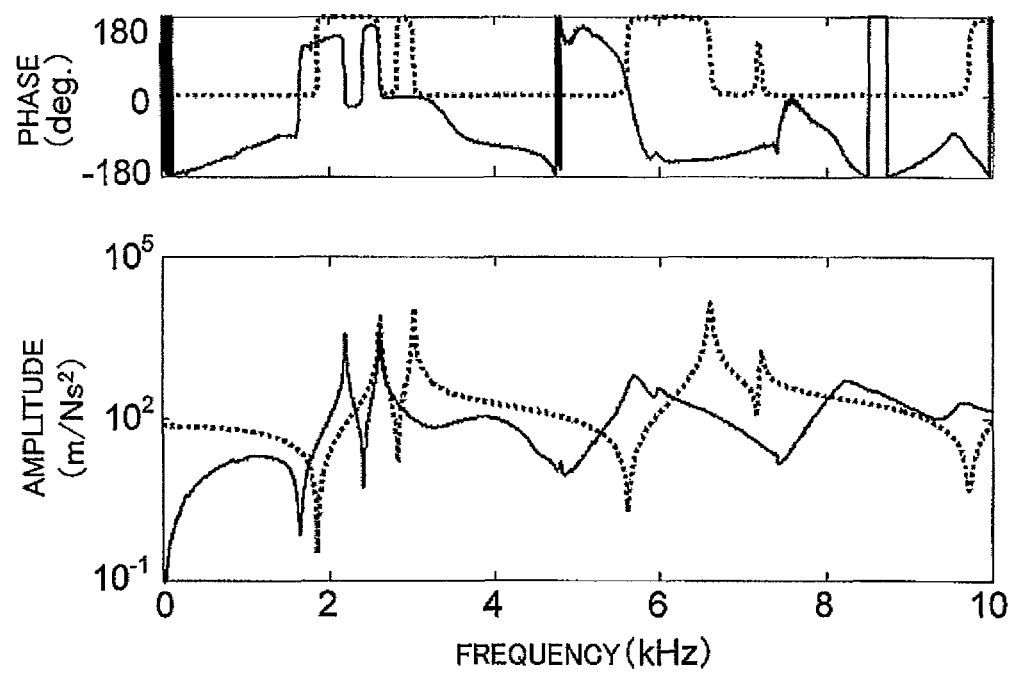
FIG. 17 is a graph showing auto FRF measured in a state where the structure is half-immersed in water, and auto FRF measured in the condition that the structure is not immersed in water.

FIG. 17 is a graph showing auto FRF ($H_{A-A}$) measured in a state where the structure 240 is half-immersed in water, and auto FRF ($H_{A-A}$) measured in the condition that the structure 240 is not immersed in water. It can be seen from this graph that the natural frequency decreases in the condition that the structure is immersed in water. Additionally, it can be seen that the damping effect also is great in a high-frequency band. This is believed to be influenced by apparent mass or viscosity induced by water.

REFERENCE 1

In Reference 1, an example in which a space in the vicinity of the surface of a structure is irradiated with a laser beam and impulse excitation sound pressure induced by LIB is applied to the structure is shown.

1. Impulse Excitation System

Figure 18:
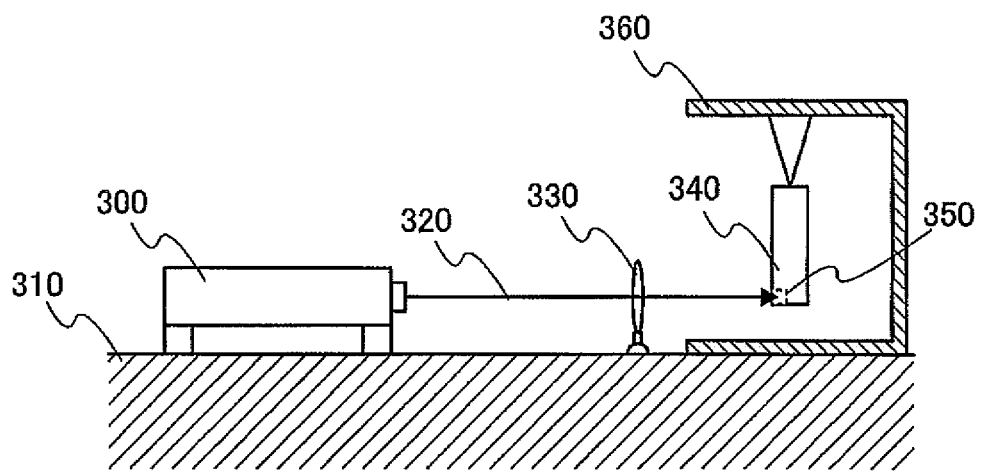
FIG. 18 is a schematic view showing the configuration of an impulse excitation system used in Reference 1.

FIG. 18 is a schematic view showing the configuration of an impulse excitation system used in the present experiment. As shown in FIG. 18, a high-output YAG pulse laser 300 (Surelite III; made by Continuum Inc.; wavelength of 1064 nm, output of 1 J, and pulse width of 5 nanoseconds) was installed on an optical table 310. A laser beam 320 from the YAG pulse laser 300 was condensed on a space in the vicinity of the surface of a structure 340 through a spherical plano-convex lens 330 (SLB-30-300P; Sigma Koki Co., Ltd.).

The structure 340 is peripherally freely supported by suspension within an anechoic box 360 (inside dimensions 580 mm×580 mm×580 mm). An accelerometer 350 (352A25; PCB Piezotronics Inc.; mass of 0.6 g, sensitivity of 0.263 mV (m/s$^2$), natural frequency of 80 kHz or more) was attached to a measurement point of the structure 340 with an adhesive. As shown in FIG. 18, the accelerometer 350 that is an output sensor was attached to the structure 340, but the input sensor for measuring the excitation force was not attached.

LIB was generated in the vicinity of the surface of the structure 340, the impulse excitation sound pressure induced by LIB being applied to the structure 340, to vibrate the structure 340. The acceleration in the vibration of the structure 340 was measured by the accelerometer 350. The object structure 340 was a flat plate (size: 100 mm×50 mm×0.5 mm) made of aluminum. The out-of-plane mode of the object structure 340 was adopted as an object to be measured.

Figure 19:
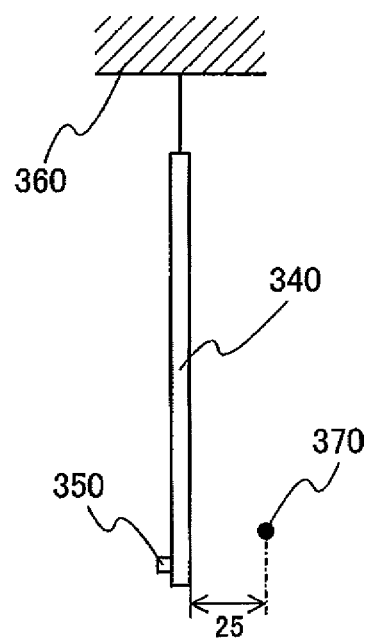
FIG. 19 is a view showing the positional relationship between a structure and a condensing point of a laser beam.

FIG. 19 is a view showing the positional relationship between the structure 340 and a condensing point 370 of a laser beam (unit: mm). The optical axis of the laser beam 320 was parallel to the planar direction of the flat-plate-like structure 340 (direction perpendicular to the plane of the sheet). As shown in FIG. 19, the interval between the condensing point 370 of the laser beam and the structure 340 was 25 mm.

The acceleration measured by the accelerometer 350 was recorded using a spectrum analyzer (A/D: NI PXI-1042Q, PXI-4472 B; National Instruments Corporation, and software: CAT-System; Catec Inc.). The frequency to be measured was more than 0 Hz and 40 kHz or less.

2. Measurement of Response

The acceleration response of the structure 340 was measured using the impulse excitation system shown in FIG. 18.

Figure 20A:
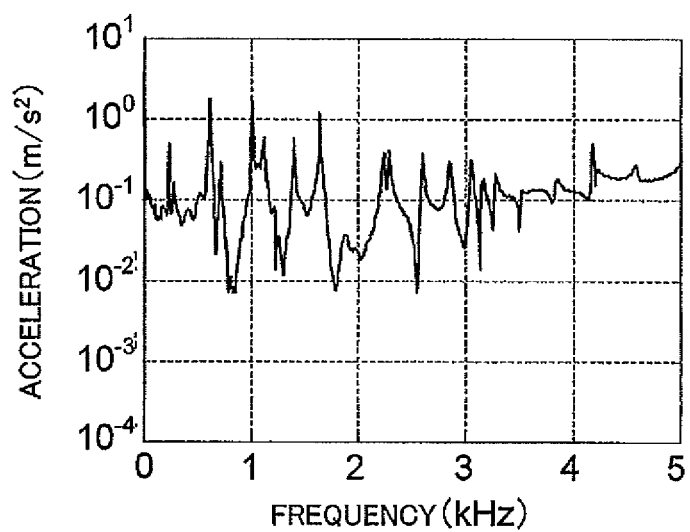
FIG. 20A is a graph showing the acceleration response of the structure when the impulse excitation sound pressure induced by laser-induced breakdown (hereinafter abbreviated as "LIB") is applied.
Figure 20B:
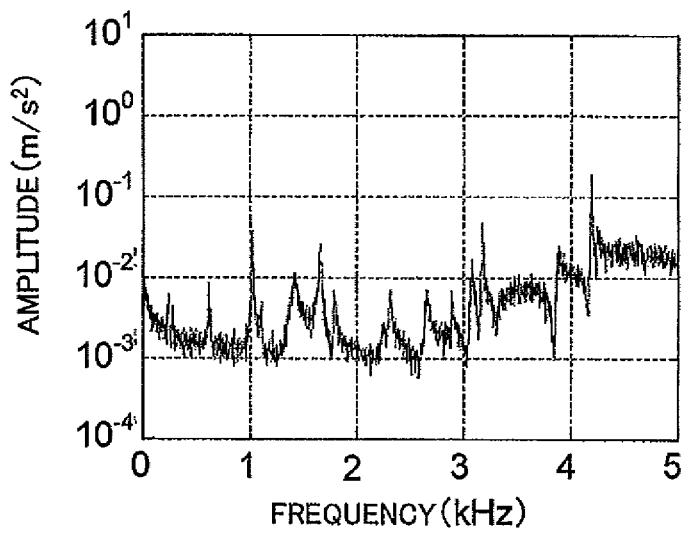
FIG. 20B is a graph showing the acceleration response of the structure when the excitation sound pressure induced by a dynamic speaker is applied.

FIG. 20A is a graph showing the acceleration response of the structure 340 when the impulse excitation sound pressure induced by LIB is applied. FIG. 20B is a graph showing the acceleration response of the structure 340 when the excitation sound pressure induced by a dynamic speaker is applied, for comparison. From these graphs, the resonant peak when the impulse excitation sound pressure induced by LIB is applied is clearer than that when the excitation sound pressure induced by the dynamic speaker is applied. It can be seen from this that measurement using the impulse excitation sound pressure induced by LIB is effective.

REFERENCE 2

In Reference 2, an example in which a structure (resin film) arranged in a vacuum is irradiated with a laser beam and the impulse excitation force induced by LA is applied to the structure is shown.

1. Impulse Excitation System

Figure 21:
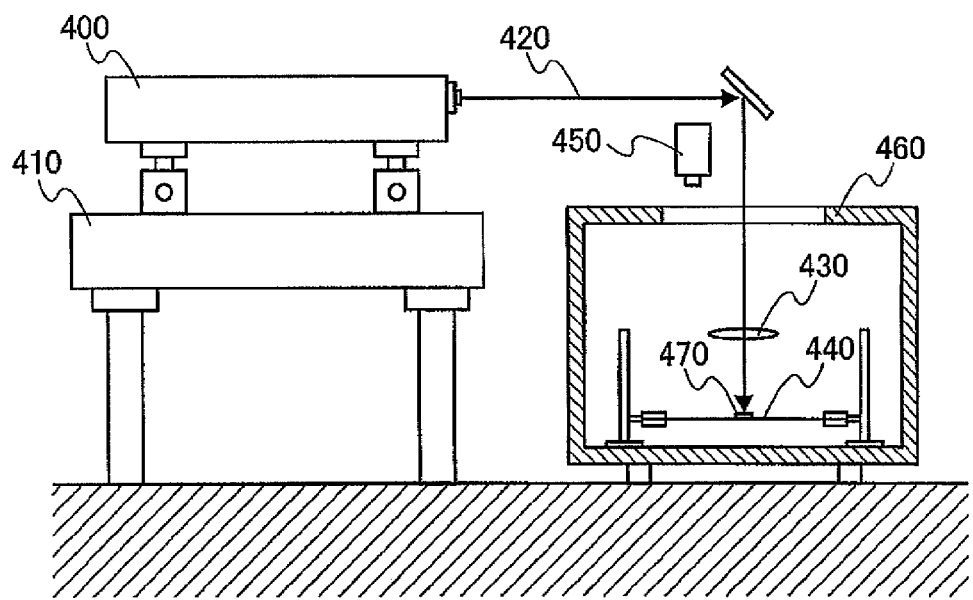
FIG. 21 is a schematic view showing the configuration of an impulse excitation system used in Reference 2.

FIG. 21 is a schematic view showing the configuration of an impulse excitation system used in the present experiment. As shown in FIG. 21, a high-output YAG pulse laser 400 (Surelite III; made by Continuum Inc.; wavelength of 1064 nm, output of 1 J, and pulse width of 5 nanoseconds) was installed on an optical table 410. A laser beam 420 from the YAG pulse laser 400 was irradiated to an aluminum plate 470 stuck on the surface of a structure 440 (resin film) through a convex lens 430 (focal distance of 100 mm).

The structure 440 (resin film) was supported in a state where tension was applied by a coil spring. The structure 440 was held in a vacuum chamber 460 (inside dimensions 360 mm×360 mm×280 mm) made of acrylic. Glass for laser transmission was inserted into a portion through which the laser beam 420 above the vacuum chamber 460 passed.

The impulse excitation force induced by LA was applied to the aluminum plate 470 stuck on the surface of the structure 440, to vibrate the structure 440. The vibration response at a measurement point of the structure 440 was measured using a laser Doppler vibrometer 450 (LV-1720; Ono Sokki, Co., Ltd.). As shown in FIG. 21, the input sensor and the output sensor are not attached to the structure 440.

The vibration response measured by the laser Doppler vibrometer 450 was recorded using a spectrum analyzer (A/D: NI PXI-1042Q, PXI-4472 B; National Instruments Corporation, and software: CAT-System; Catec Inc.).

Figure 22:
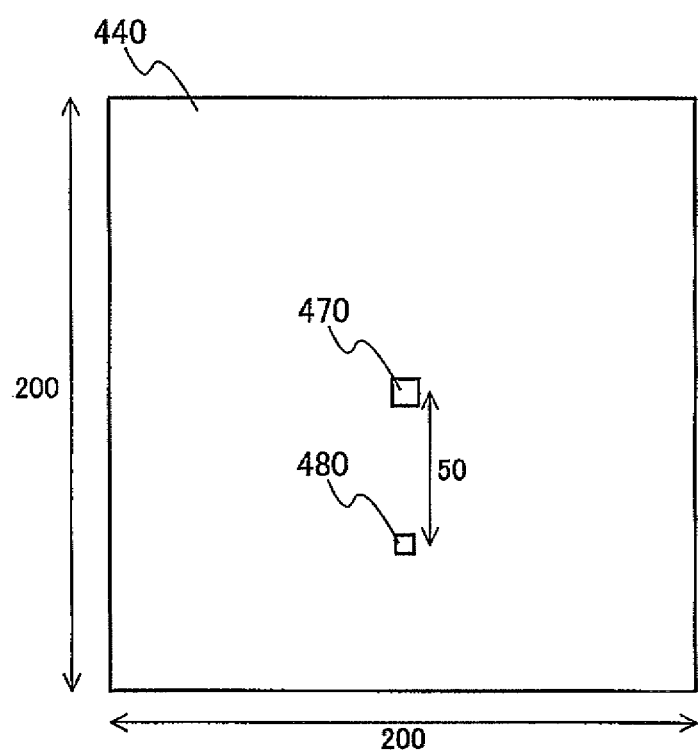
FIG. 22 is a plan view of a structure used in Reference 2.

In the present experiment, a polyimide film (Kapton; Du Pont-Toray, Inc.) was used as the structure 440. The outer shape of the polyimide film was 200 mm×200 mm, and the thickness was 50 μm. FIG. 22 is a plan view of the structure 440 used in the present experiment (unit: mm). As shown in FIG. 22, the aluminum plate 470 (13.8 mm×13.8 mm×1.5 mm) was stuck on a central portion (excitation point) of the object structure 440. Additionally, a sheet-like reflector 480 was stuck at the measurement point of the object structure in order to measure the vibration response of the object structure 440, using the laser Doppler vibrometer 450. The distance between the centers of the aluminum plate 470 and the reflector 480 was 50 mm.

2. Measurement of Response

The vibration response of the structure 440 was measured using the impulse excitation system shown in FIG. 21.

Figure 23:
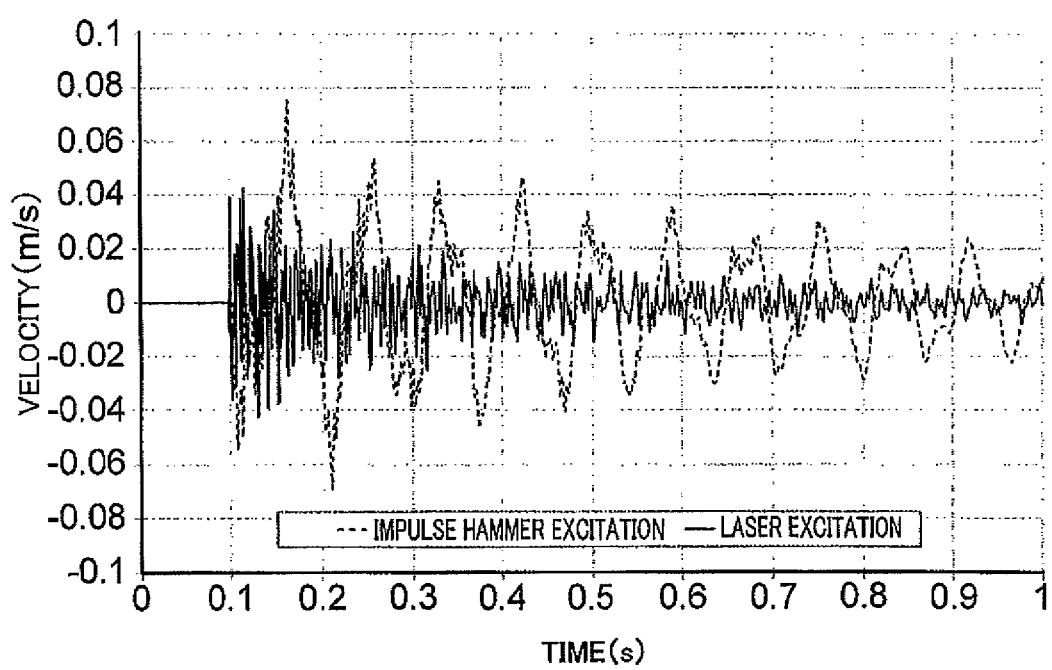
FIG. 23 is a graph showing the time history response of the structure when an impulse excitation force induced by laser ablation (hereinafter abbreviated as "LA") is applied in the atmosphere, and when an impulse excitation force induced by an impulse hammer is applied.

FIG. 23 is a graph showing the time history response of the structure 440 (resin film) when the impulse excitation force induced by LA was applied in the atmosphere, and when an impulse excitation force induced by an impulse hammer (GK-3100; Ono Sokki Co., Ltd.) was applied. The tension to the structure 440 at this time was 7.0 N, and the laser output was 600 mJ. It can be seen from this graph that, in a case where the impulse excitation force induced by LA is applied, excitation is made up to a higher-order mode and the vibration of a higher-order mode lasts for a long time, compared to the excitation induced by the impulse hammer. This is because the input duration of the impulse excitation induced by LA is very short. It can be said from this that the impulse excitation induced by LA is an ideal excitation method in exciting a lower-order mode to a higher-order mode.

Figure 24A:
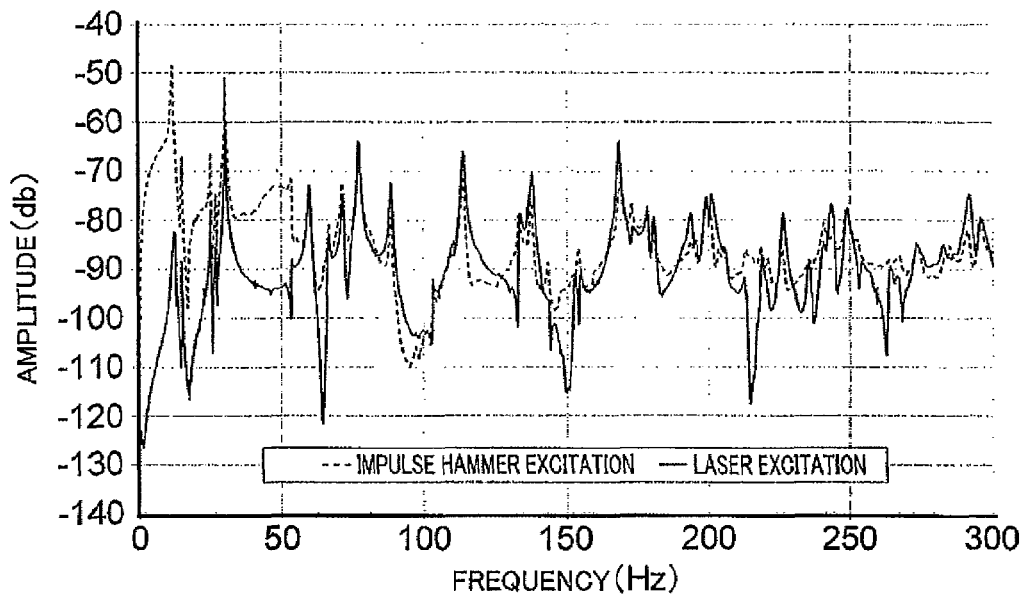
FIGS. 24A and 24B are graphs showing the power spectrum of the structure when the impulse excitation force induced by LA is applied in the atmosphere, and when the impulse excitation force induced by the impulse hammer is applied.
Figure 24B:
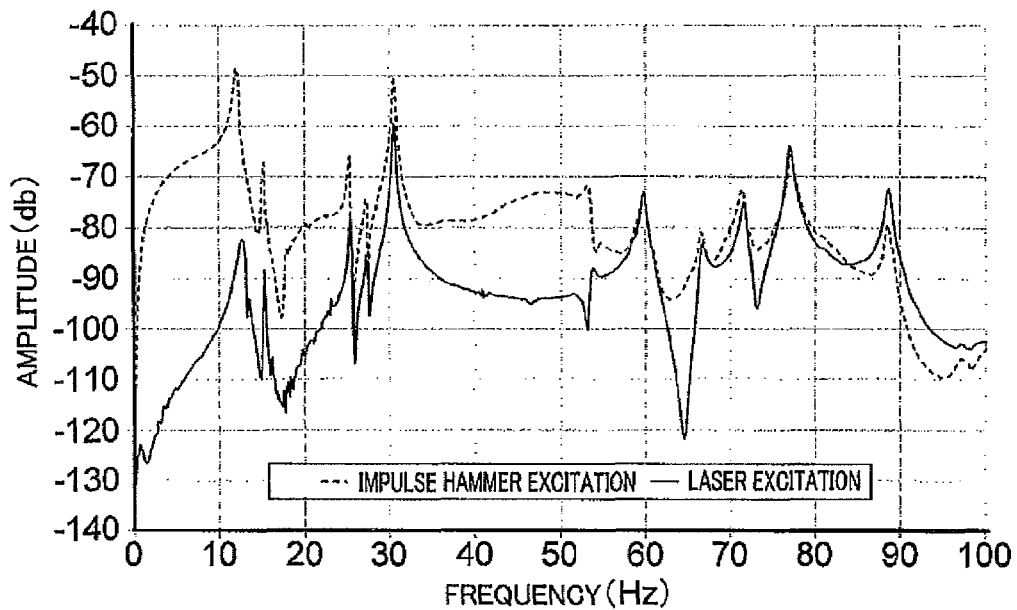

FIG. 24 is a graph showing the power spectrum of the structure 440 when the impulse excitation force induced by LA is applied in the atmosphere, and when the impulse excitation force induced by the impulse hammer is applied. FIG. 24A is a graph of a 300 Hz band (more than 0 Hz and 300 Hz or less), and FIG. 24B is a graph of a 100 Hz band (more than 0 Hz and 100 Hz or less). It can be seen from these graphs that the impulse excitation induced by LA has a sharper resonant peak and a clearer response compared to the excitation induced by the impulse hammer. Additionally, in the excitation induced by the impulse hammer, the resonant amplitude of a lower-order mode appears to a great extent, but in a higher-order mode, the resonant amplitude is small and the peak is unclear. It is believed that is because the vibration of the higher-order mode is not fully excited by the excitation induced by the impulse hammer. On the other hand, in the impulse excitation induced by LA, not only the vibration of the lower-order mode but the vibration of the higher-order mode is fully excited.

Figure 25:
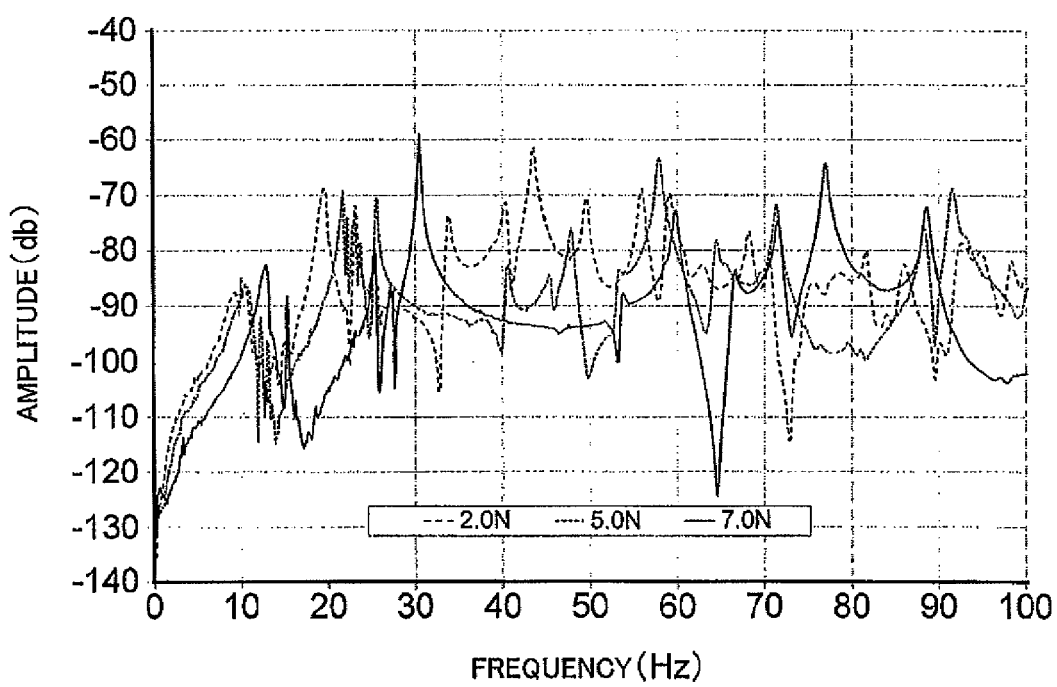
FIG. 25 is a graph showing the power spectrum of the structure when the impulse excitation force induced by LA is applied in the atmosphere.

FIG. 25 is a graph showing the power spectrum of the structure 440 when the impulse excitation force induced by LA was applied in the atmosphere. The tension to the structure 440 at this time was set to 2.0 N, 5.0 N, or 7.0 N. The laser output was 600 mJ. It can be seen from this graph that the resonant peak appears more sharply and clearly as the tension is increased. It can also be seen that the resonant frequency becomes high as the tension is increased.

Figure 26:
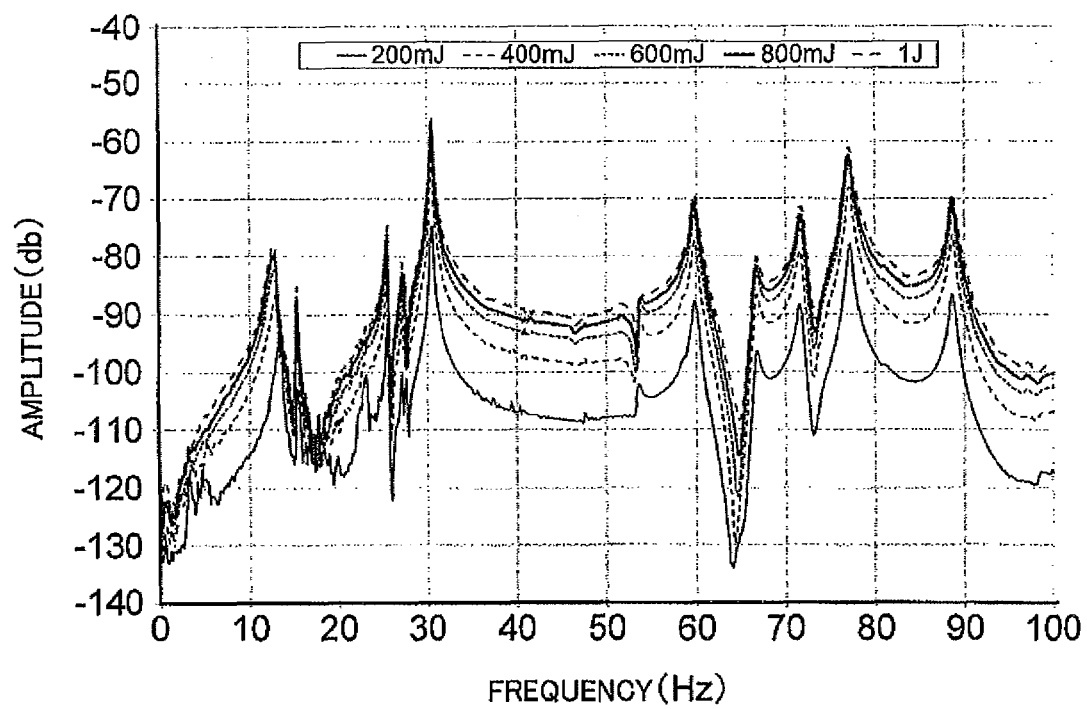
FIG. 26 is a graph showing the power spectrum of the structure when the impulse excitation force induced by LA is applied in the atmosphere.

FIG. 26 is a graph showing the power spectrum of the structure 440 when the impulse excitation force induced by LA was applied in the atmosphere. The laser output at this time was set to 200 mJ, 400 mJ, 600 mJ, 800 mJ, or 1 J. The tension to the structure 440 was 7.0 N. It can be seen from this graph that the vibration amplitude of a membrane becomes large as the laser output is increased, and the excitation force becomes large as the laser output is increased. Additionally, it can be seen that, since changes in the response amplitude caused by a difference in the laser output are almost uniform over all the frequency bands, the power spectrum of the excitation force is flat in all the frequency bands, and the magnitude thereof changes depending on the laser output.

Figure 27A:
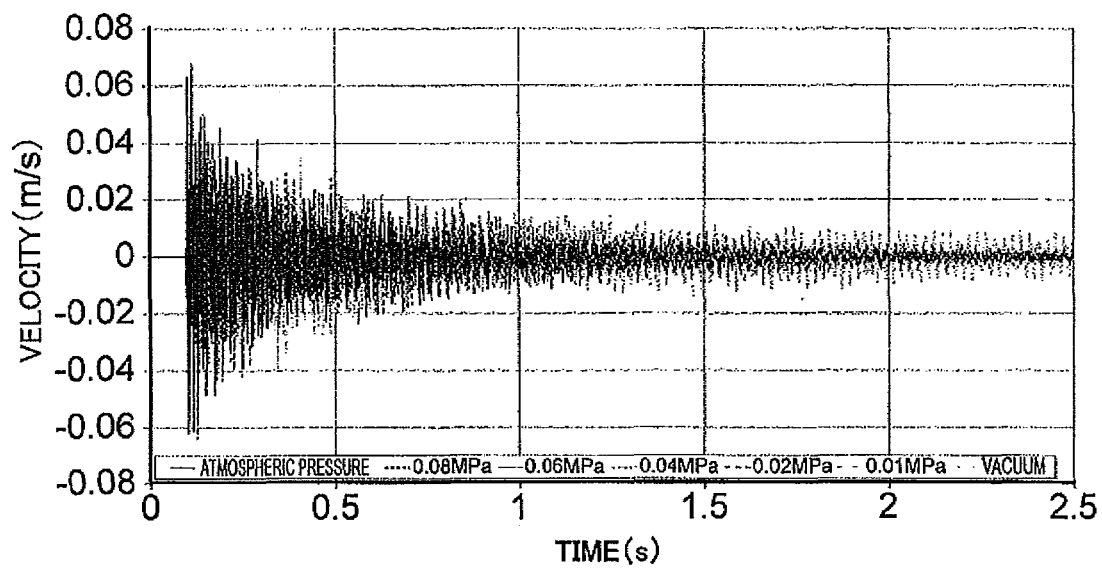
FIG. 27A is a graph showing the time history response of the structure when the impulse excitation force induced by LA is applied.
Figure 27B:
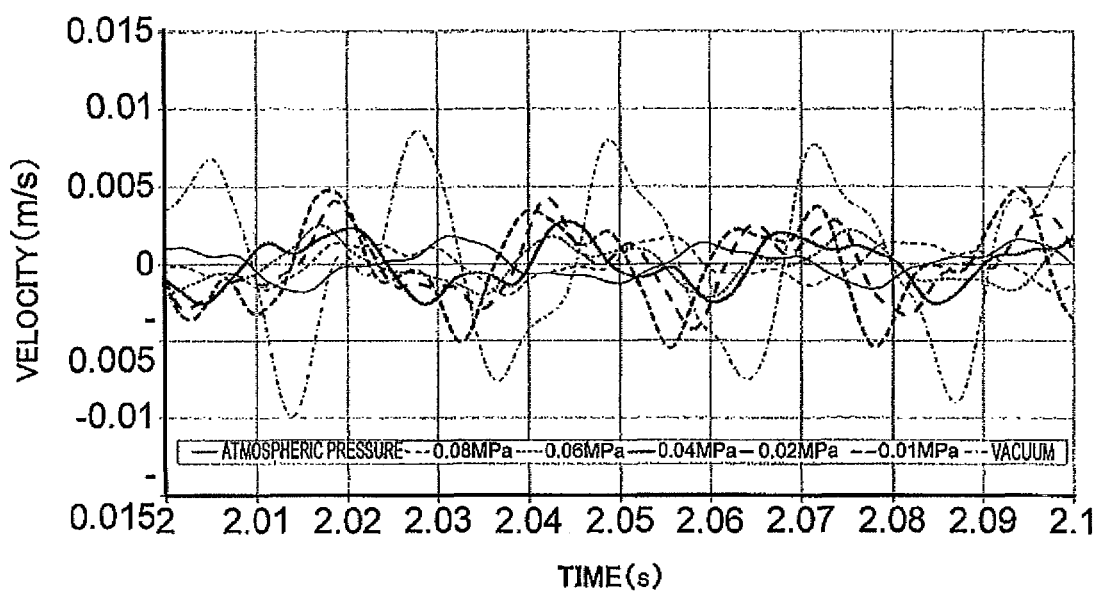
FIG. 27B is a graph showing a portion of 2.0 seconds to 2.1 seconds of the graph shown in FIG. 27A in an enlarged manner.

FIG. 27A is a graph showing the time history response of the structure 440 when the impulse excitation force induced by LA was applied. FIG. 27B is a graph showing a portion of 2.0 seconds to 2.1 seconds of the graph shown in FIG. 27A in an enlarged manner. The atmospheric pressure at this time was set to 0.1013 MPa (atmospheric environment), 0.08 MPa, 0.06 MPa, 0.04 MPa, 0.02 MPa, 0.01 MPa, or 0.00 MPa (vacuum environment). The tension to the structure 440 was 7.0 N, and the laser output was 600 mJ. It can be seen from these graphs that, as the atmospheric pressure becomes low, vibration lasts for a long time even after a given period of time has passed. It is believed that this is because air resistance decreases as the atmospheric pressure becomes low, and therefore, the damping effect to the structure 440 caused by air is reduced, and the vibration of a lower-order mode is maintained for a long time.

Figure 28A:
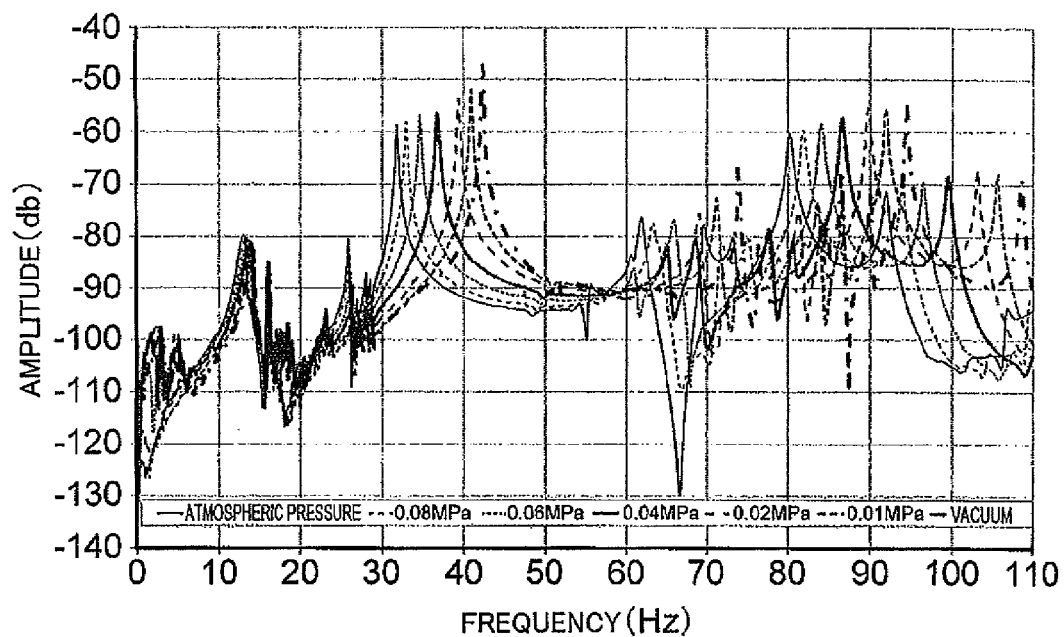
FIG. 28A is a graph showing a power spectrum of more than 0 Hz and 110 Hz or less in respective atmospheric pressures.
Figure 28B:
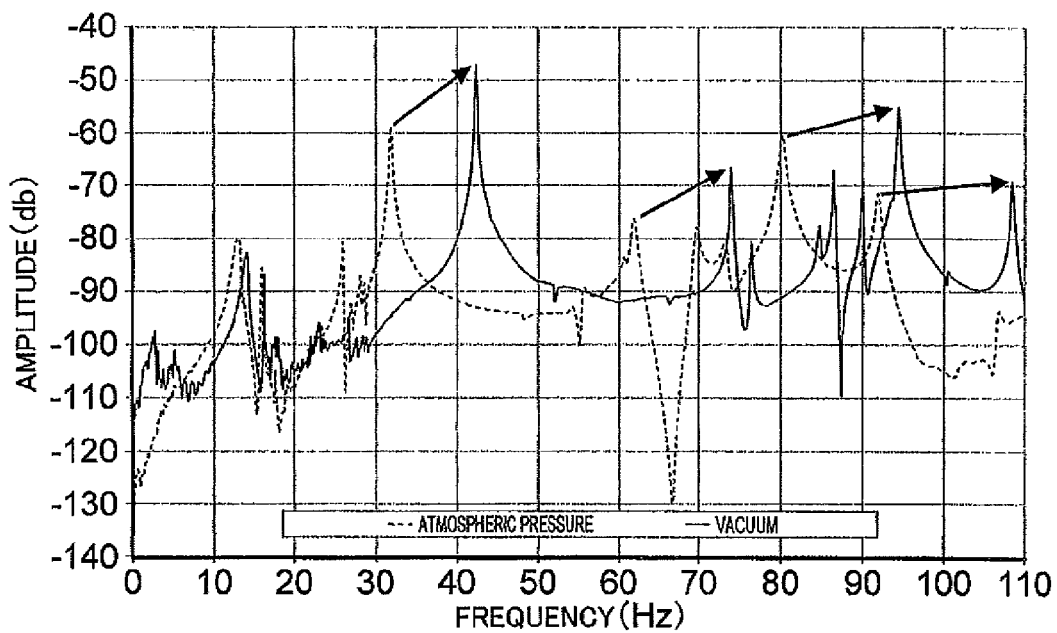
FIG. 28B is a graph showing a power spectrum of more than 0 Hz and 110 Hz or less in an atmospheric environment and a vacuum environment.

FIG. 28A is a graph showing a power spectrum of more than 0 Hz and 110 Hz or less in respective atmospheric pressures. FIG. 28B is a graph showing a power spectrum of more than 0 Hz and 110 Hz or less in an atmospheric environment and a vacuum environment. It is confirmed from these graphs that the resonant frequency of a membrane structure becomes high and the amplitude also becomes large, by reducing the atmospheric pressure (refer to arrows of FIG. 28B). It is believed that the tendency for the resonant frequency (natural frequency) to become high originates from the mass effect of air that acts on the membrane becoming small as the atmospheric pressure becomes low. Additionally, it is believed that the tendency for the amplitude to become large is produced when the damping effect of air that acts on the membrane structure as the atmospheric pressure becomes low is reduced.

Generally, in a structure made of a material, such as a metal, having a large density compared to air, air hardly affects the vibration response. However, since the membrane has a very light and flexible property in the membrane structure, it is believed that the air mass on the surface of the membrane has a great influence. As shown in FIG. 28B, it can be seen that the resonant frequency in the vacuum environment becomes about 10 to 15 Hz higher than the atmospheric environment, in a measurement frequency band. Additionally, it is believed that the resonance of a small sharp peak obviously seen in a band of 70 to 90 Hz in the vacuum environment appears due to reduction in the damping effect, in a mode where an excitation point or a response point is close to a node.

It can be seen from the above that the non-contact type measurement using the impulse excitation induced by LA and the laser Doppler vibrometer is very effective in a vibration test of a light, thin, and flexible structure as in the membrane structure. Additionally, it can be seen that it is not necessary to install devices for excitation and measurement in the vacuum chamber with respect to vibration tests under respective atmospheric pressure conditions and a vacuum condition, and the vibration tests in such environments are easily realized by installing all of those functions out of the vacuum chamber.

The disclosure of Japanese Patent Application No. 2010-136185, filed Jun. 15, 2010, including the specification, drawings and abstract, is incorporated herein by reference in its entirety.

INDUSTRIAL APPLICABILITY

According to the invention, a non-contact excitation type measurement system without an input sensor that comes into contact with a structure can be realized. Accordingly, the invention brings about ground-breaking effects for vibration measurement of MEMS, measurement in a minimum space, or the like. Of course, the invention also contributes to a countermeasure against vibration or noise of a washing machine that is a general home appliance, and studies for silencing of refrigerators or air-conditioners. Additionally, with respect to the tires of a car, for example, it is possible to exactly evaluate pattern noise resulting from a tread pattern or to evaluate the vibration properties of the tires during actual traveling. Additionally, the method for measuring vibration properties in the invention can also evaluate the vibration properties of underwater structures, such as an underwater robot, and an inflatable space structure made of a lightweight and flexible resin film or the like.

Moreover, according to the invention, non-contact of input measurement or input/output measurement is possible. Therefore, testing in institutions and facilities in which direct contact with people is difficult can also be safely and easily performed. For example, metal fatigue is one cause of accidents in aircraft, nuclear power stations, or the like. Particularly, fatigue fracture in aircraft, nuclear generators, cars, trains, or the like leads to major accidents that also threaten human lives. According to the invention, through a simple system, it is possible to detect malfunctions, such as fine metal fatigue, and prevent these major accidents in advance, by non-contact vibration tests even in plant portions with a concern for radiation contamination.

REFERENCE SIGNS LIST

100, 200, 300, 400 High-output YAG pulse laser
110, 210, 310, 410 Optical table
120, 220, 320, 420 Laser beam
130, 230, 330, 430 Convex lens
140, 240, 340, 440 Structure
150, 170, 350 Accelerometer
160, 260 Rigid body block
250, 450 Laser Doppler vibrometer
270 Air cushion
360 Anechoic box
370 Condensing point
460 Vacuum chamber
470 Aluminum plate
480 Reflector

The invention claimed is:

1. A method for generating vibration and measuring vibration properties, which may include frequency response function (FRF), of a structure with an output sensor, comprising:
   (A) supporting the structure peripherally freely and positioning a portion of the structure in one selected from the group consisting of liquid, gas and a vacuum;
   (B) positioning the output sensor in a configuration wherein the output sensor is unattached or attached to the structure;
   (C) irradiating a surface of the structure or a vicinity of the surface of the structure with a pulse laser beam from a pulse laser oscillator, to produce an impulse excitation force induced by laser ablation or an impulse excitation sound pressure induced by laser induced breakdown;
   (D) vibrating the structure through application of the impulse excitation force or the impulse excitation sound pressure;
   (E) measuring acceleration response or velocity response at a measurement point on the surface of the structure with an accelerometer, a laser Doppler vibrometer or a laser displacement gage;
   (F) estimating the relationship between the laser intensity and the impulse excitation force or the impulse excitation sound pressure through application of the rigid pendulum method, and calculating magnitude F of the impulse excitation force or the impulse excitation sound pressure applied to the structure, the estimating comprising preparing a rigid body block freely supported, irradiating a surface of the rigid body block or a vicinity of the surface of the rigid body block with a pulse laser beam to produce an impulse excitation force induced by laser ablation or an impulse excitation sound pressure induced by laser induced breakdown, applying the impulse excitation force or the impulse excitation sound pressure to the excitation point of the rigid body block and measuring the acceleration response or the velocity response of the measurement point of the rigid body block; and
   (G) calculating a complex Fourier spectrum normalized by the magnitude F comprising dividing a complex Fourier spectrum of the frequency amplitude and the vibration amplitude obtained from the acceleration response or the velocity response, by the magnitude F of the impulse excitation force or the impulse excitation sound pressure in order to determine the vibration properties of the structure.

2. The method of claim 1, further comprising measuring application time L of the impulse excitation force or the impulse excitation sound pressure corresponding to the amount of time the impulse excitation force or the impulse excitation sound pressure is applied to the structure and correcting properties of the complex Fourier spectrum normalized by the magnitude F with the application time L.

\* \* \* \* \*